(12) United States Patent
Brånemark et al.

(10) Patent No.: US 9,067,057 B2
(45) Date of Patent: Jun. 30, 2015

(54) PERCUTANEOUS GATEWAY, A FIXING SYSTEM FOR A PROSTHESIS, A FIXTURE AND CONNECTING MEANS FOR SIGNAL TRANSMISSION

(75) Inventors: Rickard Brånemark, Mölndal (SE); Max Jair Ortiz Catalan, Göteborg (SE)

(73) Assignee: INTEGRUM AB (SE)

( * ) Notice: Subject to any disclaimer, the term of this patent is extended or adjusted under 35 U.S.C. 154(b) by 0 days.

(21) Appl. No.: 13/818,635

(22) PCT Filed: Aug. 22, 2011

(86) PCT No.: PCT/SE2011/051004
§ 371 (c)(1),
(2), (4) Date: Feb. 22, 2013

(87) PCT Pub. No.: WO2012/026870
PCT Pub. Date: Mar. 1, 2012

(65) Prior Publication Data
US 2013/0166009 A1  Jun. 27, 2013

(30) Foreign Application Priority Data

Aug. 24, 2010 (SE) .................................... 1050869

(51) Int. Cl.
*A61B 5/04* (2006.01)
*A61N 1/05* (2006.01)
*A61F 2/28* (2006.01)
*A61F 2/76* (2006.01)
(Continued)

(52) U.S. Cl.
CPC ................. *A61N 1/05* (2013.01); *A61F 2/2814* (2013.01); *A61F 2/72* (2013.01); *A61F 2/76* (2013.01); *A61F 2/78* (2013.01); *A61F 2002/30668* (2013.01); *A61F 2002/6827* (2013.01); *A61F 2002/705* (2013.01); *A61F 2002/7615* (2013.01); *A61F 2002/7887* (2013.01)

(58) Field of Classification Search
CPC .... H04R 25/606; H04R 25/60; H04R 25/604; A61F 11/04; A61F 2002/183; A61F 2250/0002
USPC ................. 607/3, 55–57, 115–117, 136–137; 600/25, 377, 378
See application file for complete search history.

(56) References Cited

U.S. PATENT DOCUMENTS

| 5,562,670 A | 10/1996 | Braanemark |
| 5,984,859 A | 11/1999 | Lesinski |

(Continued)

FOREIGN PATENT DOCUMENTS

WO    WO 9855049    12/1998

OTHER PUBLICATIONS

International Search Report for International Application No. PCT/SE2011/051004, mail date Jan. 26, 2012, 7 pages.

*Primary Examiner* — Rex R Holmes
(74) *Attorney, Agent, or Firm* — Foley & Lardner LLP

(57) ABSTRACT

A percutaneous gateway is provided for permanently transmission between inside of a body and outside of the body, comprising an implant (10) adapted to be at least partly anchored in a bone (1). The implant (10) has a transmission means (30) that allows a long-term stable communication through a transmitting device (20) adapted to extend from an implantable component (90) through the bone (80) to a device (91) at the outer end (3) of the percutaneous gateway.

12 Claims, 18 Drawing Sheets

(51) Int. Cl.
*A61F 2/78* (2006.01)
*A61F 2/72* (2006.01)
*A61F 2/30* (2006.01)
*A61F 2/68* (2006.01)
*A61F 2/70* (2006.01)

(56) References Cited

U.S. PATENT DOCUMENTS 6,840,919 B1  1/2005  Haakansson
2009/0248165 A1* 10/2009 Lin et al. ............... 623/17.19

* cited by examiner

Fig. 18
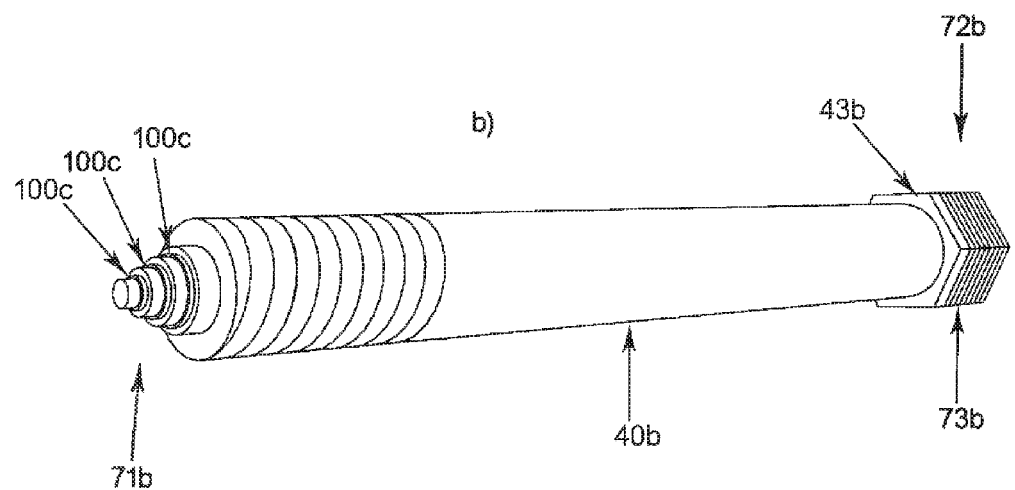
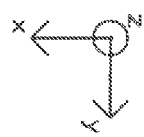
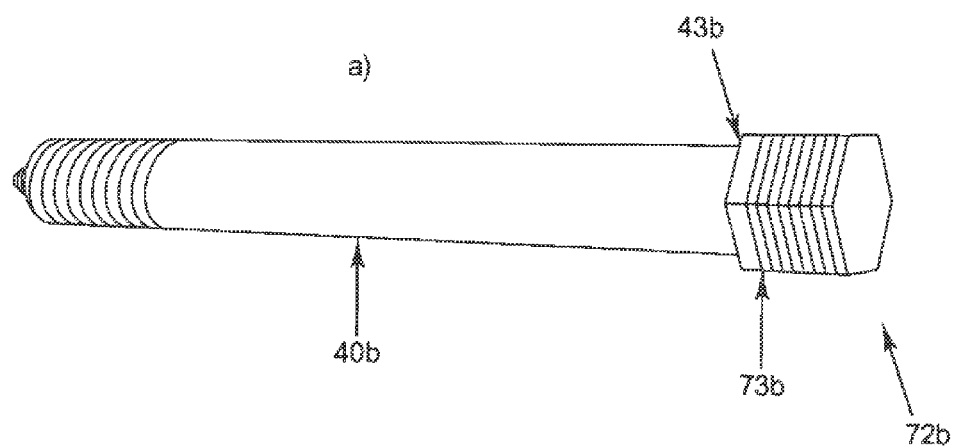

Fig. 19
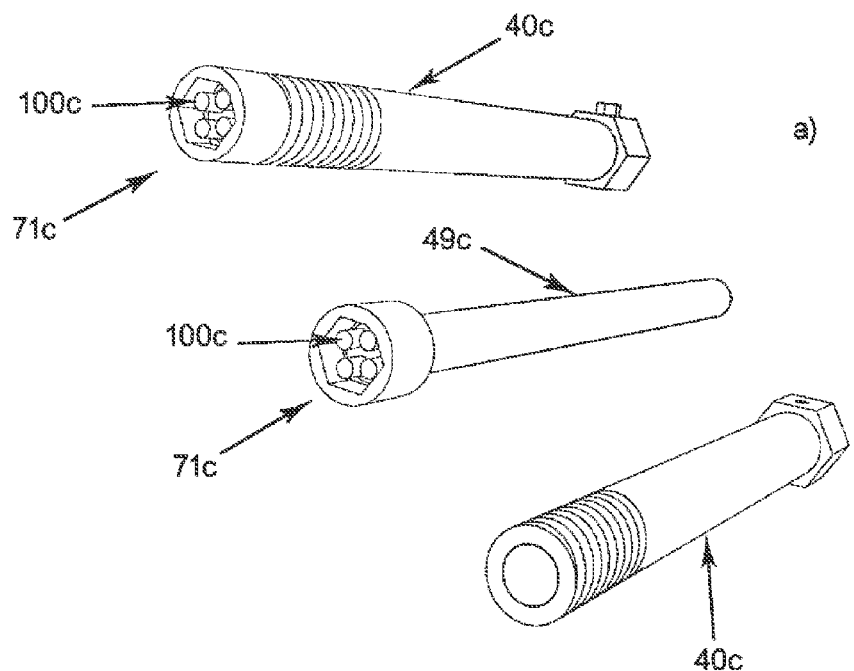
a)
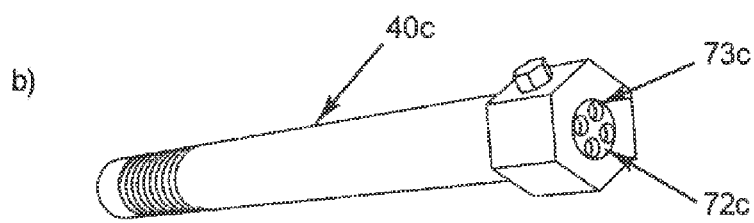
b)
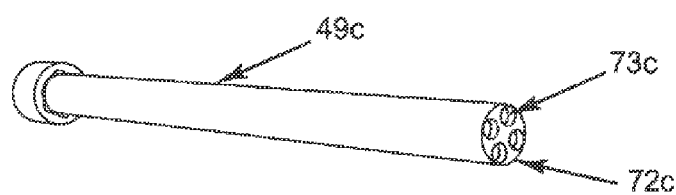
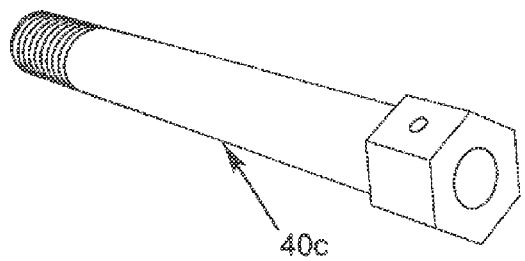

PERCUTANEOUS GATEWAY, A FIXING SYSTEM FOR A PROSTHESIS, A FIXTURE AND CONNECTING MEANS FOR SIGNAL TRANSMISSION

TECHNICAL FIELD

The present invention relates to an apparatus, especially for attaching a prosthesis to a human body, as defined in the preamble of the attached claim 1.

Further, the present disclosure generally refers to a percutaneous gateway for transmitting signals between an inside of a body and an outside of the body.

Furthermore, the present disclosure refers to a fixing system being a part of the percutaneous gateway for anchoring, communicating or/and controlling a prosthesis in a bone of, e.g., a limb.

Furthermore, the present disclosure refers to a fixture which may be associated to a fixing system for anchoring a bone anchored robotic prosthesis.

In addition, the present disclosure refers to in-line connectors for connecting different parts of a transmitting device for transmitting the electrode signals in a fixing system of the type mentioned above.

Finally, the present disclosure refers to a method for implanting a fixing system.

BACKGROUND OF THE INVENTION

Ever since the use of implantable devices, its permanent access has been an issue. There are several problems from sending or retrieving data to how to power such devices. For instance, a surgery to replace batteries from neuroprostheses or pacemakers would be avoided if direct connection to the devices would be possible. Different component such as electrodes, biosensors or more complex electronic devices to measure different biological parameters would benefit from a direct connection to out of the body devices such as stimulators, recorders, robotic prosthesis, etc. A stimulator could be used from outside to body for pain treatment by sending electric impulses to implanted electrodes if such link would be safe and permanently available.

A Human-Machine-Gateway (HMG) is, for example, required for achieving a natural control of a robotic prosthesis. "Natural" herein is referred to as produce control in the same way that an intact physiological system. This means coordinated and simultaneous movements of different degrees of freedom. Furthermore, "natural" also implies that the input signals must come from muscles that originally are meant to produce the intended movement or/and from nerves that controlled those muscles. Fine movements performed by actuators in the robotic prosthesis require a long-term stable and defined connection to the human body that provides input control signals.

Accordingly, a bone anchored robotic prosthesis may be fixed on an amputation stump of a limb by an implant (fixture) which is implanted in a bone inside the stump. Accordingly, bone anchored prosthesis are attached directly to the bone and not attached to the body via the skin of the stump.

The fixture may preferably be implanted into the bone based on the principle of osseointegration. Osseointegration implies direct contact between the fixture and the bone. That means the fixture as the anchoring element is surgically inserted into the bone of the amputation stump. After approximately six months a skin penetrating connection component (abutment) is attached to the fixture. Then, the patient's prosthesis is attached to the outer part of the abutment.

For a natural control of the bone anchored robotic prosthesis several further components are required. For example, input and output signals may be generated and transmitted to actuators and from sensors in the robotic prosthesis and to electrodes inside the limb. The required nerve and/or muscle signals as the control input are detected by biosensors, for example, nerve electrodes or muscle electrodes, and transmitted to a control circuit or amplifier located inside the robotic prosthesis or the limb itself. Furthermore, signals from the robotic prosthesis are processed in a control circuit and feedback to the patient. Therefore, the user of such a robotic prosthesis may naturally control the actuators provided in the robotic prosthesis in accordance to the signals detected in the electrodes and used the feedback sent from the prosthesis for a close loop control.

The lack of good algorithm and control systems were once the principal issues for accomplishing a complex prostheses control. Nowadays several researches have shown that it is possible to identify fingers and hand positions using different pattern recognition algorithms such as artificial neural networks (ANNs), support vector machines (SVM), hidden markov models (HMM), wavelets, etc. Manipulation of different devices like robotic arms using myoelectric signals as information source and SMV as control algorithm has been proved as a feasible technology as well. However, these examples and all known experiments have been short-term implementations.

Now that pattern recognition algorithms and hardware for a real time control are available, the major issue is the long-term stability of the biosignals. The stability is heavily related on how the biosignals are acquired which brings in other two major problems. The first one is the amount of signals that are possible to retrieve due the physical limitations. The second problem is related to how natural it would be for the patient to produce signals for a given propose.

The following are some of the issues in a practical implementation of a prosthetic control based in pattern recognition algorithms. These problems are mostly attributed to the surface electrodes.

Electrodes cannot remain placed indefinitely due to skin related issues.

Electrodes cannot be placed consistently in the same spot after removing the prosthesis.

A different placement of the electrode will required a retraining of the control system.

The signal changes dramatically with the environmental conditions, i.e. sweating.

Artefacts are very easily generated due to limb movement and electrode liftoff.

A patient needs to have a minimum level of myoelectric signals to become a candidate for using a myoelectric prosthesis. This is not always the case depending on the amputation level and the muscle surface left for the electrodes placement.

A wide limb surface area needs to be covered to have enough control signals.

Muscle imbalance could be created if the electrodes are wrongly placed resulting in muscles being more exercised than others. In the long run, this will cause that the big muscle's signal masks the other one. Muscle imbalance can also cause prosthesis socket instability.

Clinical studies have shown that acceptance of prostheses is difficult to achieve, especially the myoelectric type where there are more possibilities of failure.

Lack of feedback to the patient.

Unnatural control. The same group of muscles control different units in a sequential manner instead of individual muscles controlling specific actions simultaneously.

EP 0 595 782 B1 discloses an anchoring element (fixture) for supporting a prosthesis, said anchoring element having essentially the form a screw and being arranged for a connection by its outer end portion to said prosthesis and by its opposite inner end portion to be inserted and anchored in bone tissue.

WO 03/000161 A1 discloses a system of implantable sensor/stimulation devices that is configured to communicate with a prosthetic device, e.g., an artificial limb, via a wireless communication link, preferably bidirectional. By communicating between the implantable devices coupled to neural pathways within a human and motor/sensor interfaces in the prosthetic device, a machine and a human/machine interface is established to replace an absent limb.

GB 2 445 869 A discloses a percutaneous prosthetic device comprising at least one soft tissue fixture adapted to be fixed to the musculotendinous soft tissue of a residual limb and a percutaneous anchor for an external prosthesis that is fixedly coupled directly or indirectly, to the bone of the residual limb in use, the percutaneous anchor having a percutaneous sleeve component. Furthermore, the device comprises at least one transmission means allowing transmission of one or more signals between the soft tissue fixture and external prostheses. The transmission means is guided outside the bone through the percutaneous anchor to the external prosthesis. The signal or signals relate to contraction and/or relaxation of muscle in the residual limb and do not consider signals form nerves. Preferably the transmission means comprises a connecting means connecting the soft tissue fixture and an external prosthesis in use. The connecting means may comprise a mechanical or an electrical connector. Preferably the connecting means comprises a seal connection within the percutaneous component to provide an effective barrier between the internal and external environment.

CN 1545988 discloses a method for controlling a prosthesis by means of biological electrical signals in human bodies. Accordingly, an upper end of an implantation member is inserted into a remnant bone of an amputee's stump. The implantation member comprises a hole located in a portion of the implantation member being not implanted into the bone, the hole comprising an inner end exiting into the soft tissue. Afterwards, the steps of connecting the lower projecting member with a artificial limb, implanting the electrodes into the nerve-tract or muscle hank in the soft tissue, leading the contact conductor to the external signal conditioning device through the through-hole of the not implanted portion of the implantation member, carrying out magnification and filtration to the signal collected by the electrodes, mapping the signal into the control message for artificial limb motion, the control signal feeding to the motor to drive the artificial limb, are performed.

U.S. Pat. No. 6,034,295 discloses an implantable device, such as a femoral head prostheses, with a body of biocompatible material shaped to suit its medical function, which forms in internal cavity and has open apertures that lead from the cavity to the outside. The cavity serves to receive biological material into which the tissue that surrounds the implanted device is intended to grove through the apertures. The device is provided with at least two electrodes, at least one of which is located in the cavities based apart from the inside of the body that forms the cavity. The electrodes are provided with an arrangement for supplying a low frequency alternating voltage, so that by means of the supplied voltage a low frequency electrical alternating field and a low frequency alternating current, whereby the tissue grow is promoted, are created inside the cavity.

FR2802083 discloses an implantable device to anchor natural or prosthetic ligaments. It is a fully implanted device with an inside cavity to secure the prosthetic ligament. The implant is used to keep the graft in place and it is especially designed for the knee articulation.

SUMMARY OF THE INVENTION

An object of the present invention is to provide an improved signal transfer or communication between one or a plurality of implantable components or devices, such as biosensors, e.g. electrodes, glucose measuring devices, or stimulating devices etc, and one or a plurality of external devices, such as a robotic prosthesis for controlling the robotic prosthesis or health monitoring recorders.

The above-mentioned object of the present invention is attained by an apparatus, especially for attaching a prosthesis to a human body, comprising an anchoring element for fixation in a bone tissue, especially human bone tissue, the anchoring element defining a longitudinal axis. The anchoring element comprises at least one first through-hole substantially extending in the direction of the longitudinal axis, and the anchoring element comprises first attachment means for attaching the anchoring element to the bone tissue and second attachment means for directly or indirectly attaching the anchoring element to the prosthesis. The anchoring element comprises at least one seat provided in the first through-hole, wherein the seat is adapted to receive and hold a sealing device adapted to be positioned in the first through-hole, the sealing device being adapted to divide the first through-hole into at a first compartment and a second compartment, and wherein the sealing device is adapted to separate the first compartment from the second compartment in a sealing manner. The anchoring element may have a first end portion and a second end portion opposite the first end portion. The anchoring element may be elongated. Each compartment may be adapted to house signal transmission means. Each compartment may substantially extend in the direction of the longitudinal axis. The through-hole may extend from a first opening to a second opening. When the sealing device is positioned in the seat, the first compartment may extend from the sealing device to the first opening, and the second compartment may extend from the sealing device to the second opening.

By "in a sealing manner" in this context means that the sealing device is adapted to seal the first and second compartments off from one another, such that a body fluid or bacteria cannot pass from one of the compartment to the other.

By the present invention, body fluid from the bone or soft body tissue is prevented from reaching the exterior, and bacteria from the environment outside the human body is efficiently prevented from reaching the region inside the human body where e.g. the anchoring element is in contact with bone and soft tissue and where the implantable components or devices are implanted, which would have been the case if a continuous through-hole in the anchoring element were in contact with both the interior and the exterior of the human body. By the present invention, bacteria or body fluid cannot pass from one compartment to the other. By the present invention, improved signal transmission or communication between one or a plurality of implantable components or devices, such as biosensors, e.g. glucose measuring devices, or stimulating devices etc, and a robotic prosthesis for controlling the robotic prosthesis is attained. By the solution of the present invention, a long-term stable signal transmission or communication is provided, which has a reduced sensitivity to internal and external stress. By the solution of the present invention, the attachment or anchorage of the anchoring element to the human body tissue is long-term stable. Further, by the present invention, the mechanical stress on the implantable electrodes, components or devices from the soft tissues is minimized or reduced.

According to an advantageous embodiment of the apparatus according to the present invention, the anchoring element has a first end portion and a second end portion opposite the first end portion, and when the sealing device is positioned in the seat the first compartment extends from the sealing device in the direction towards the first end portion of the anchoring element, and the second compartment extends from the sealing device in the direction towards the second end portion of the anchoring element. However, each compartment may extend in other ways.

According to a further advantageous embodiment of the apparatus according to the present invention, the first through-hole has an inner wall, at least a portion of the inner wall forms the seat, and the sealing device is adapted to be attached to the inner wall of the first through-hole. This is an efficient way to form the seat, whereby the above-mentioned effects are further enhanced.

According to another advantageous embodiment of the apparatus according to the present invention, the portion of the inner wall of the through-hole, which forms the seat, has at least one internal thread, the sealing device has an outer wall portion having least one external thread, and the at least one inner thread of the seat is adapted to engage the least one outer thread of the sealing device. This is an efficient way to seal between the outer wall of the sealing device and the inner wall of the first through-hole. However, other designs of the seat are possible, for example the seat may comprise one or a plurality of axial grooves or projections, the seat may provide a snap function in relation to the sealing device, the seat, e.g. in the form of a surface, may be adapted to receive an adhesive, such as glue etc.

According to still another advantageous embodiment of the apparatus according to the present invention, the seat is adapted to removably, or detachably, attach the sealing device to the anchoring element. This is an efficient way to facilitate the maintenance and the installation of the apparatus. Alternatively, the sealing device may be permanently seated in the seat.

According to yet another advantageous embodiment of the apparatus according to the present invention, the apparatus comprises first signal transmission connection means for connection to first signal transmission means adapted to extend in the first compartment, wherein the first signal transmission connection means is connectable to second signal transmission means adapted to extend in the second compartment and to extend from the sealing device to second signal transmission connection means for connection to at least one implantable component. Each signal transmission means may comprise an electric conductor, such as a wire or cable, an optical fibre, a magnetic link, a mechanical communication link etc, or a plurality thereof. The first signal transmission connection means may comprise a connector or a male connector as disclosed below. The first signal transmission means may comprise a first signal transmitting part as disclosed below. The second signal transmission means may comprise a second signal transmitting part as disclosed below. The second signal transmission connection means may comprise a connector or a male connector as disclosed below. However, other suitable means are possible.

According to an advantageous embodiment of the apparatus according to the present invention, the sealing device is adapted to separate the first signal transmission means from the second signal transmission means in a sealing manner. By "in a sealing manner" in this context means that the sealing device is adapted to seal the first and second transmission means off from one another, such that a body fluid or bacteria cannot pass from one of the transmission means to the other.

According to a further advantageous embodiment of the apparatus according to the present invention, the first signal transmission connection means is adapted to be located in the first compartment. Hereby, the above-mentioned effects are further enhanced.

According to another advantageous embodiment of the apparatus according to the present invention, the first signal transmission connection means is attachable to, attached to and/or adjoins the sealing device. Hereby, the above-mentioned effects are further enhanced.

According to still another advantageous embodiment of the apparatus according to the present invention, the sealing device defines a longitudinal axis and comprises at least one second through-hole substantially extending in the direction of the longitudinal axis, and the first signal transmission connection means is adapted to at least partly engage the second through-hole in a sealing manner. As the first signal transmission connection means engages the second through-hole, an efficient seal is provided between the inner wall of the secondthrough-hole of the sealing device and the exterior of the first signal transmission connection means. Additional sealing means, e.g. adhesive, e.g. glue, may also be applied to seal, or supplement the seal, between the first signal transmission connection means and the sealing device. Hereby, the above-mentioned effects are further enhanced.

According to yet another advantageous embodiment of the apparatus according to the present invention, the apparatus comprises an abutment defining a longitudinal axis and having a first end portion and a second end portion opposite the first end portion, wherein the abutment comprises at least one third through-hole substantially extending in the direction of the longitudinal axis, wherein the second attachment means are adapted to attach the abutment to the anchoring element, and wherein the abutment is mountable to the prosthesis. This is an efficient way to facilitate the maintenance and the installation of the apparatus. Hereby, the above-mentioned effects are further enhanced. The abutment may be elongated.

According to an advantageous embodiment of the apparatus according to the present invention, the third through-hole is adapted to house at least a part of the first signal transmission means extending therethrough from the first signal transmission connection means to a third signal transmission connection means for connection to the prosthesis. Hereby, the above-mentioned effects are further enhanced. The third signal transmission connection means may comprise a connector or a head connector as disclosed below. However, other suitable means are possible.

According to a further advantageous embodiment of the apparatus according to the present invention, the first attachment means comprise at least one external thread. Alternatively, the first attachment means may have other designs, and may for example comprise a rough friction surface etc.

According to another advantageous embodiment of the apparatus according to the present invention, the first attachment means are adapted for fixation in the bone tissue.

According to yet another advantageous embodiment of the apparatus according to the present invention, the second attachment means comprise at least one internal thread. Alternatively, the second attachment means may have other designs, and may for example comprise a rough friction surface etc.

The above-mentioned object of the present invention is also attained by an apparatus, especially for attaching a prosthesis to a human body, comprising an anchoring element for fixation in a bone tissue, the anchoring element defining a longitudinal axis. The anchoring element comprises at least one first through-hole substantially extending in the direction of the longitudinal axis, and the anchoring element comprises first attachment means for attaching the anchoring element to the bone tissue and second attachment means for directly or indirectly attaching the anchoring element to the prosthesis, wherein the apparatus comprises a sealing device adapted to be positioned in the first through-hole and to divide the first through-hole into at a first compartment and a second compartment, and wherein the sealing device is adapted to separate the first compartment from the second compartment in a sealing manner. The positive technical effects of this apparatus correspond to the effects mentioned in connection with the above-mentioned apparatus. The anchoring element may have a first end portion and a second end portion opposite the first end portion.

The above-mentioned object of the present invention is also attained by the use of the apparatus according to any of the appended claims 1 to 18, or any of the above-mentioned embodiments of the apparatus, for supporting a prosthesis or part thereof in bone tissue.

Various examples of the different parts and features and further advantages of the above-mentioned embodiments of the apparatus according to the present invention are disclosed below.

According to a first aspect of the present disclosure, a percutaneous gateway for transmitting signals between an inside of a body and an outside of the body may comprise an implant as a signal transmitting device. The implant may be adapted to be at least partly anchored in a bone. Furthermore, the implant may have an implant through-hole which may have an inner end and an outer end. The inner end may open into the bone and the outer end may end outside the body. The signal transmitting device may be adapted to extend from the inner end to the outer end of the implant through-hole and to transmit signals between these ends.

With the percutaneous gateway according to the first aspect of the present invention, signals may be transmitted from implanted devices, for example, bio-sensors, nerve-based electrodes, muscle based electrodes to a device outside the body. Furthermore, also signals and power may be supplied from the outside to the devices installed inside the body. The implant allows to feed the signal transmitting device through the implant directly to the sensors passing through the bone. Therefore, there is no need for an extra percutaneous passage of the signal transmitting means. Furthermore, the implant is fixed in the bone. Accordingly, the implant is long-term stable anchored to the residual stump. Therefore, the skin may perfectly seals around the implant and remaining bone allowing a long-term implantation with a low risk of infection. In a standard percutaneous passage of wires, the skin will not seal around the wires and there will be a constant risk of infection. A key feature of this invention is that the sealing interface between skin and bone is not disturbed since the exit to the soft tissue is through the bone. This solution is also convenient since the leads are protected from mechanical stress by being inside the bone for a longer distance than in the constantly moving soft tissue.

As a first exemplary embodiment, the percutaneous gateway may further comprise a sealing device being adapted to be inserted in the implant through-hole or be already embedded as part of the implant. Accordingly, the signal transmitting device may be adapted to be fixed by the sealing device and to be fed through the sealing device. Furthermore, the sealing device may be adapted to seal an outside of the sealing device to the implant through-hole and an inside of the sealing device to the signal transmitting device. The sealing may allow preventing body fluid and bacteria from passing the sealing device if the sealing device is inserted into the implant through-hole or it is already embedded in the implant.

Accordingly, the percutaneous gateway prevents body fluids, bacteria and such, from passing through the implant through-hole. That means, body fluids may be prevented from flowing from the inner end of the implant through-hole to the outer end, and bacteria may be prevented from entering into the bone from the outer end of the first through-hole because the sealing screw seals and closes the first through-hole. Furthermore, the transmitting device may be fixed (housed) by the sealing device in a sealed manner.

According to a second aspect of the present disclosure, a fixing system for anchoring a robotic prosthesis on a bone of a limb may be a part of the percutaneous gateway. Accordingly, the implant may comprise a fixture adapted to be at least partly anchored in the bone. The fixture may include a first through-hole having the inner end located opening into the bone. Furthermore, the through-hole may have an outer end directed to the outer end of the implant through-hole. Furthermore, the signal transmitting device (e.g., a cable or connector) may be adapted to extend from the inner end to the outer end of the first through-hole and to transmit electric signals between these ends.

With the fixing system according to the second aspect of the present invention, a robotic prosthesis may be fixed to the bone while at the same time signals may be transmitted between the inside of the body to the outside of the body. Accordingly, it is possible to transmit signals from implanted electrodes through the bone and the first through-hole of the fixture using a feedthrough connector to the outer end of the fixture.

Accordingly, the signal transmitting means may safely, long-term stable guided and fixed inside the fixture. Therefore, the fixing system provides fixing means (fixture) for the robotic prosthesis including a possibility for feeding through the signal transmitting means. Accordingly, the fixing system is compact and modular.

As a first exemplary embodiment, the above fixing system may further comprise a sealing device (e.g., a sealing screw) adapted to be inserted in the first through-hole of the fixture. Furthermore, also the sealing device may comprise a (second) through-hole. The signal transmitting device may be adapted to be fixed by the sealing device and to be fed through the second through-hole of the sealing device. Furthermore, the sealing device may be adapted to seal an outside of the sealing device to the first through-hole and an inside of the sealing device to the signal transmitting device. Therefore, preferably body fluid and bacteria are prevented from passing the sealing device which is inserted in the first through-hole.

Accordingly, the fixing system prevents body fluids and bacteria from passing through the through holes. That means, body fluids may be prevented from flowing from the inner end of the through hole (bone opening side) to the outer end, and bacteria may be prevented from entering into the bone from the outer end of the first through hole because the sealing device (screw) seals and closes the first through hole. Furthermore, the transmitting device may be safely fixed by the sealing device.

Furthermore, the above fixing system according to the first exemplary embodiment may further comprise an abutment fixing device (abutment screw). The implant may further comprise an abutment. Accordingly, the abutment fixing device may be adapted to fix the abutment in the first through hole of the fixture. Furthermore, also the abutment fixing device may be fixed to the fixture. The abutment may comprise a (third) through-hole extending between the outer end of the implant through-hole located outside the body and the outer end of the first through-hole of the fixture. That means, the third through-hole may elongate the first through-hole of the fixture to the outer end of the implant. Furthermore the abutment may be adapted to provide a connection between the robotic prosthesis and the fixture. Furthermore, the signal transmitting device may be adapted to be fed through the third through-hole of the abutment. Furthermore, the abutment may be a percutaneous abutment.

Accordingly, the abutment may provide a percutaneous passage of the fixing system. That means, the abutment is preferably the element of the fixing system which protrudes from the stump and serves as a fixing terminal for the robotic prosthesis but also connects the robotic prosthesis to the bone anchored fixture. The fixed abutment is a proved solution for a long-term stable percutaneous passage.

Furthermore, the third through-hole of the abutment may provide the passage for the signal transmitting device (cables or connector). Accordingly, an extra percutaneous passage for the transmitting device may be avoided completely thereby preventing a path for virus and bacteria and providing a long-term stability. The problem of the percutaneous passage may be solved by using an abutment made of titanium as a bone extension. Such an abutment has approved long-term stability.

Furthermore, in the above fixing system according to the first exemplary embodiment the fixture may further comprise a first fixing section (e.g., a first female thread) and a second fixing section (e.g., a second female thread) in the first through-hole. Furthermore, the sealing device may be adapted to be fixed in the second fixing section. The abutment fixing device may comprise a fourth through-hole. Furthermore, the abutment fixing device may be fixed in the first fixing section of the fixture. The fixture, the abutment, the abutment fixing device and the sealing device may be arranged on a common axis in the longitudinal direction. Furthermore, the signal transmitting device may be fed through the fourth through-hole of the abutment fixing device.

Accordingly, the respective elements of the fixing system may be positioned into each other and fixed with each other. Therefore, the fixing system may be a stable and compact system being able to accommodate the respective transmitting device and to transmit the forces applied to the abutment (as the fixing terminal for the robotic prosthesis) into the bone.

Furthermore, in the above fixing system according to the first exemplary embodiment the signal transmitting device may further comprise a first signal transmitting part and a second signal transmitting part. The first signal transmitting part may have a first connector (e.g., an in-line female connector) on one end. The second signal transmitting part may have a second connector (e.g., an in-line male connector) on one end. The first and the second connector may be adapted to be connected with each other. The first signal transmitting part may be adapted to be located in the fourth inner hole of the abutment fixing device. The second signal transmitting part may be adapted to be fed through the sealing device and the first through-hole to the bone. Furthermore, the second signal transmitting part may be adapted to be fed through a fifth through-hole in the bone from the inner end of the first through-hole inside the bone to an outside of the bone but inside a soft tissue of the limb.

Accordingly, for example, the abutment fixing device housing the first signal transmitting part may be removed or replaced without necessarily removing or replacing the sealing device and/or the second transmitting part. Accordingly, the different elements of the fixing system may be removed or replaced without removing or replacing other elements of the fixing system. Furthermore, the fixing system may be assembled easily. Therefore, a modular fixing system is provided.

Furthermore, in the above fixing system according to the first exemplary embodiment the first signal transmitting part comprises a third connector at the other end. Furthermore, also the second signal transmitting part comprises a fourth connector at the other end. The third connector may be adapted to be connected to an outside device, and the fourth connector may be adapted to be connected to an implanted device or sensor.

Accordingly, the fixing system allows signals to be transmitted from, for example, implanted electrodes through the bone, the fixture, the sealing device and the abutment fixing device to the control circuitry or amplifier of the robotic prosthesis. The control circuitry may also be implanted in the soft tissue or inside the fixture. The different transmitting parts may be disconnected and connected when replacing or assembling the different elements. A control circuit can be placed either inside the limb or outside the limb. The transmission may be bidirectional, stimulation of nerves and muscles according to sensing elements in the robotic prosthesis may be considered.

Accordingly, it is ensured that the connector for the electrodes and the respective cable(s) providing the connection between the fourth connector and the second connector may feed through the fixture. Furthermore, the shielding prevents electromagnetic interference (EMI).

Furthermore, in the above fixing system according to the first exemplary embodiment the first connector may be a longitudinal in-line female connector having contact sockets and female insulating means arranged in the fourth through-hole of the abutment fixing device. Furthermore, the second connector may be a longitudinal male connector having contact elements and insulating elements adapted to protrude into the first connector. Accordingly, a signal transmission between the first and second connector may be provided by connecting the respective contact sockets with the contact elements by inserting the contact elements into the respective contact sockets.

Accordingly, a high number of different signals may be transmitted via different contacts sockets and elements arranged in a line (in-line). The connectors may allow a compact and integrated design. Accordingly, the male connector may be a connector pin and the female connector may be a contact stack. Furthermore, the male contact elements and contact sockets may easily be connected and allow long-term stable contact.

Furthermore, alternatively to the in-line above connectors the first and second connectors may be connected by a parallel connection.

This may allow low manufacturing costs as parallel connection are industrial standard products.

Furthermore, in the above fixing system according to another exemplary embodiment the third connector may be an in-line or a circular parallel connector, and the fourth connector may be an in-line connector or a parallel connector.

According to a third aspect of the present disclosure, a fixture as an anchoring element for fixing a robotic prosthesis on bone, may comprise an inner section. The inner section may be adapted to be anchored inside the bone. Furthermore, the fixture may comprise a through-hole extending along a longitudinal axis. The through-hole may have an inner end located in the inner section. The inner end may open into the bone. An outer end of the through-hole may be located on the opposite end with respect to the longitudinal axis. Furthermore, may be a fixing portion is located in the through-hole. The fixing portion may be adapted to fix the robotic prosthesis at the fixture and to accommodate a sealing device. The sealing device may be adapted to seal an outside of the sealing device to the through-hole and an inside of the sealing device to a transmitting device such that body fluid and bacteria are prevented from passing the inserted sealing device in the first through-hole.

The fixture (anchoring element) may used in the fixing system according to the second aspect of the present disclosure. The fixture may allow fixation of a robotic prosthesis and feeding through signal transmitting means from inside the bone to the outside. Furthermore, the fixing portion may be adapted to house the sealing device to seal and close the through-hole of the fixture such that body fluid and bacteria are prevented from passing the sealing device.

Furthermore, in the above fixture according to the first exemplary embodiment, the fixing portion may be divided into a first fixing section and a second fixing section. The first fixing section may be adapted to fix the robotic prosthesis at the fixture. The second fixing section may be adapted to accommodate the sealing device. Preferably, the first fixing section is at least partly a first female thread having a first inside diameter. Furthermore, the first fixing section is preferably arranged with a third distance from the inner end in the direction to the outer end. The second fixing section is preferably at least partly a second female thread having a second inside diameter and being arranged with a second distance from the inner end of the fixture in the direction to the outer end. Preferably the third distance of the first fixing section to the inner end is greater than the second distance of the second fixing section to the inner end. Furthermore, the inside diameter of the first fixing section is preferably larger than the inside diameter of the second fixing section.

Accordingly, the robotic prosthesis may be fixed independently from the sealing device and the signal transmitting device in the fixture. Therefore, the different elements may be replaced independent from each other. Furthermore, the assembling order may defined by the above arrangement.

According to a fourth aspect of the present disclosure, a cylindrical in-line female connector for connecting signal transmitting parts of a signal transmitting device in a fixing system for anchoring a robotic prosthesis on a bone may extend on a longitudinal axis and may be adapted for insertion of an in-line male connector. The female contact sockets may have a through-hole for inserting an in-line male connector. Furthermore, the female contact sockets may be arranged in-line on the longitudinal axis. The insulating means may have a through-hole and may be arranged on the longitudinal axis in-line between the female contact sockets. Furthermore, the in-line female connector may comprise transmitting means for transmitting signals from the respective contact sockets to a first end of the in-line female connector. Furthermore, the transmitting means may be insulated from the other female contact sockets.

Accordingly, with the in-line female connector a predetermined number of different signals may be transmitted to a corresponding in-line male connector, wherein the cylindrical in-line female connector has a compact design. Accordingly, the in-line female connector may be adapted to be inserted in, for example, a longitudinal screw body.

Furthermore, the in-line female connector according to the first exemplary embodiment may further comprise a longitudinal groove provided in the longitudinal direction on an outside surface of the contact sockets and the insulating means. Furthermore, the in-line female connector may comprise an annular groove on the outside surface of each contact socket, respectively. In the in-line female connector, may be each transmitting means is guided in the longitudinal groove from the respective contact socket to the first end. Furthermore, each transmitting means may be electrically connected to the respective contact socket in the annular groove.

Accordingly, the above in-line female connector may provide the advantage that the cables for connecting the different contacts sockets may safely guided on the surface of the in-line female connector without increasing the outside diameter of the in-line female connector. Furthermore, the contact between the transmitting means and the respective contact socket may be ensured by the connection in the annular groove.

Furthermore, the in-line female connector according to the first exemplary embodiment may be sealed and/or shielded.

Accordingly, entering of body fluids into the in-line female connector and/or electromagnetic interferences may be prevented.

According to a fifth aspect, the present disclosure is directed to an in-line male connector for connecting signal transmitting parts of a signal trans-mitting device in a fixing system for anchoring a robotic prosthesis on a bone. The in-line male connector may extend on a longitudinal axis and may be adapted to be inserted into an in-line female connector. Furthermore, the in-line male connector may comprise at least two contact elements and an insulating element. Both, the contact elements and the insulating element may have a through-hole and may be arranged in-line on the longitudinal axis. The insulating element may be arranged between the contact elements. Furthermore, the in-line male connector may comprise transmitting means for transmitting signals from the respective contact elements to a first end of the in-line male connector. Each trans-mitting means may be arranged in the through-hole and may be insulated from the other contact elements.

Accordingly, a predetermined number of different signals may be transmitted to a corresponding in-line female connector, wherein the cylindrical in-line male connector has a compact and, in particular, thin design.

In a sixth aspect, the present disclosure is directed to a method for implanting a fixing system for anchoring a robotic prosthesis on a bone. The method may comprise implanting a fixture having a first through-hole in a bone.

Furthermore, the method comprises drilling a through-hole from an inner end of the fixture from inside the bone to outside the bone but inside a soft tissue of a limb. Furthermore, the method may comprise inserting a transmitting device inserted in a sealing device from an outer end of the fixture into the first through-hole and the through-hole of the bone. As a further step, the method may comprise sealing the first through-hole by the sealing device. As a further step, the method may comprise fixing an abutment for fixing the robotic prosthesis in the fixture by an abutment fixing device.

The above method provides a long-term stable implantation of a fixing system for robotic prosthesis having simple surgical steps and ensuring a high success rate. The different steps may be interchanged.

It is to be understood that both the foregoing general description and the following detail description are exemplary and explanatory only and are not restrictive of the disclosure.

Other features and aspects of this disclosure will be apparent to the skilled person based up on the following description, the accompanying drawing and the attached claims.

The above-mentioned features and embodiments of the apparatus, gateway, fixing system, fixture, connectors and method, respectively, may be combined in various possible ways providing further advantageous embodiments.

The most advanced commercial myoelectric prostheses are limited to a proportional control (speed or strength) of basic movement (e.g. opening and closing the hand). They all use surface electrodes to read myoelectric signals from relatively strong muscle contractions which is inefficient and unnatural for the patient. Unnatural control causes most of myoelectric prostheses rejections.

A solution to obtain long-term stable signals is the use of implantable electrodes and biosensors. Implantable electrodes may used to overcome the most of the problems mentioned in the background, in particular, the signal quality is more consistent over time and less affected by surrounding noise. Furthermore, the use of nerve-based implantable electrodes allows to obtain signals to several muscles from a single nerve.

Furthermore, a solution to obtain stable and stronger signals from implantable electrodes is the use of amplifiers. Such amplifiers may be integrated in a housing of the implantable electrode but not necessarily.

Furthermore, feedback such as slip or force signal to the patient may be transmitted from the prosthesis to the muscles and nerves to provide a "natural" feeling for the patient. Accordingly, a stimulation of the muscles and nerves could be provided.

These ideas bring another big issue, namely signal transmission between the inside of the body and the outside of the body.

The present disclosure is directed, at least in part, to improving or overcoming one or more aspects of the prior percutaneous Human-MachineGateways for transmitting signals between an inside of a body and an outside of the body. In particular, the present disclosure may be directed to provide a fixing system, a fixture, connectors and a method for implantation of such a fixing system for bone anchored robotic prostheses allowing a permanent long-term stable transmission of signals between, for example, a prosthesis outside the limb and devices inside of a limb.

Although the idea of using signals generated in nerves and muscles to control a robotic prostheses is known since the 1960's, currently there is no long-term stable implementation of such control. This is mainly because surface recordings are highly environmental dependent, which is a problem that is solved using implanted electrodes. The use implanted electrodes has the major issue of how to permanently collect their recordings. The use of percutaneous passage of wires must be avoided because it is a path for virus and bacteria. The invention here described is the solution to this problem.

A substantial an important difference to all the known state-of-art is the fact that the invention here described does not disturbs the skin sealing by exiting to the soft tissue through the bone. The skin sealing tight to the bone and percutaneous bone extension, is the key for a long-term stability.

BRIEF DESCRIPTION OF THE DRAWINGS

FIG. 18 is a perspective view of an abutment fixing device according to a third embodiment, in a) seen from the side, and in b) seen from the side and bottom, FIG. 19 is a perspective view of an abutment fixing device according to a fourth embodiment, in a) seen from the bottom side, and in b) seen from the top side

DETAILED DESCRIPTION OF THE DRAWINGS

Figure 1:
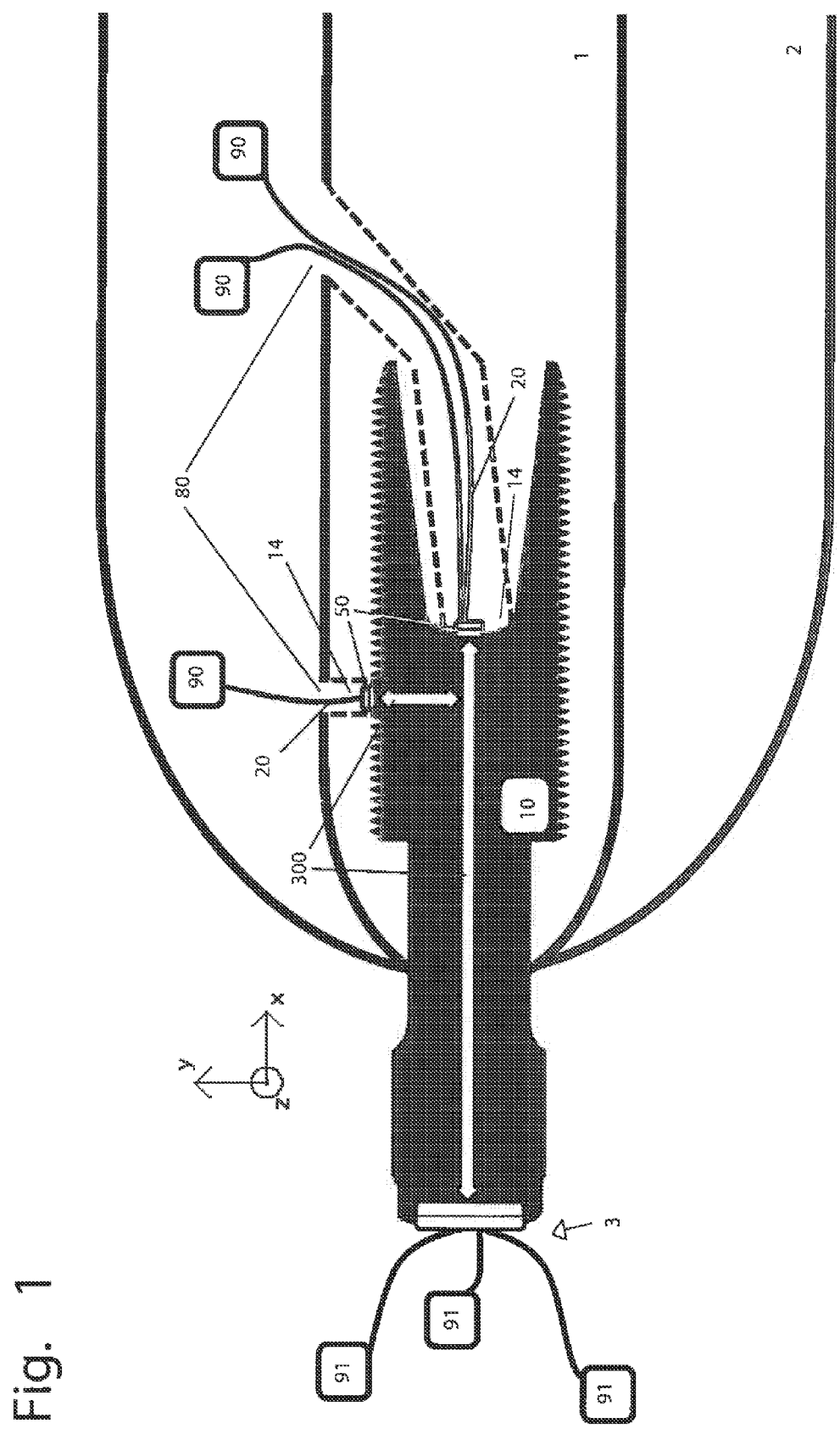
FIG. 1 shows a general overview of a percutaneous gateway according to a first embodiment.

In the following, embodiments are described with reference to the drawings.

Overview of the Percutaneous Gateway

An overview over a percutaneous gateway according to a first aspect of the present disclosure will shortly be described with reference to FIGS. 1 and 2. The percutaneous implant (10) preferably comprises a fixture 10a adapted to be anchored in a bone 1 of, for example, a limb 2, and an abutment 30 as a percutaneous part extending from an inside of the body to an outside of the body.

However, the implant is not limited to the two part design. Accordingly, the implant may be a single element or may comprise more than two elements.

The fixture 10a is preferably completely implanted in the bone 1. An inner end of the percutaneous abutment 30 is preferably fixed inside an outer end 15 of the fixture 10a. An outer end of the percutaneous abutment 30 projects from the stump or limb 2 (or body) to the outside of the body.

Preferably, the abutment 30 and the fixture 10a, respectively, comprise at least one through-hole 11, 31. These through-holes 11, 31 are constituting an implant through-hole extending from an inner end 14 opened to an inside of the bone 1 to an outer end 3 outside of the body. Accordingly, at least one signal or power transmitting device 20, for example, a cable, a light trans-mitting fiber, a magnetic link and so on may be fed through the implant through-hole 11, 31 from the outside of the body to the inner end 14 inside the bone 1.

Furthermore, the bone 1 may have at least one through-hole 80 in extension of the implant through-hole(s) 11, 31 such that the signal transmitting device 20 may be guided from the implant through-hole 11, 31 to the soft tissue 5.

Preferably, a sealing device 50 which may be inserted into the implant through-hole 11, 31 is adapted to prevent bacteria from entering into the bone 1 and body fluids from exiting the body via the implant through-hole 11, 31.

Preferably, at least one connector (coupling) 66, 67 may be provided inside the soft tissue 5 and/or one connector (coupling) 71, 61 may be provided inside the implant through-hole 11, 31 which is connectable to at least one implanted device 90.

Implanted devices 90 are, for example, biosensors such as glucose measuring devices, or stimulating devices, drug delivery devices, electrodes and so on which may be supplied with energy from the outside or batteries and may transmit and received signals to devices outside the body. Therefore, may be a bidirectional connection is provided. Furthermore, the implanted devices 90 may constitute a muscular interface and/or a neural interface.

Outside the body, a stimulator, a robotic prosthesis, a bio-signal recorder etc as an outside device 91 may be connected to the transmitting device 20 such that the devices 91 outside the body (outside devices) are connected to devices 90 inside the body via the percutaneous gateway in a long-term stable manner. However, different devices may also be housed in the percutaneous gateway or in the limb.

Overview of the Fixing System According to the First Embodiment

A first exemplary embodiment of the implanted and assembled percutaneous gateway including a fixing system is described with reference to the drawings.

Figure 2:
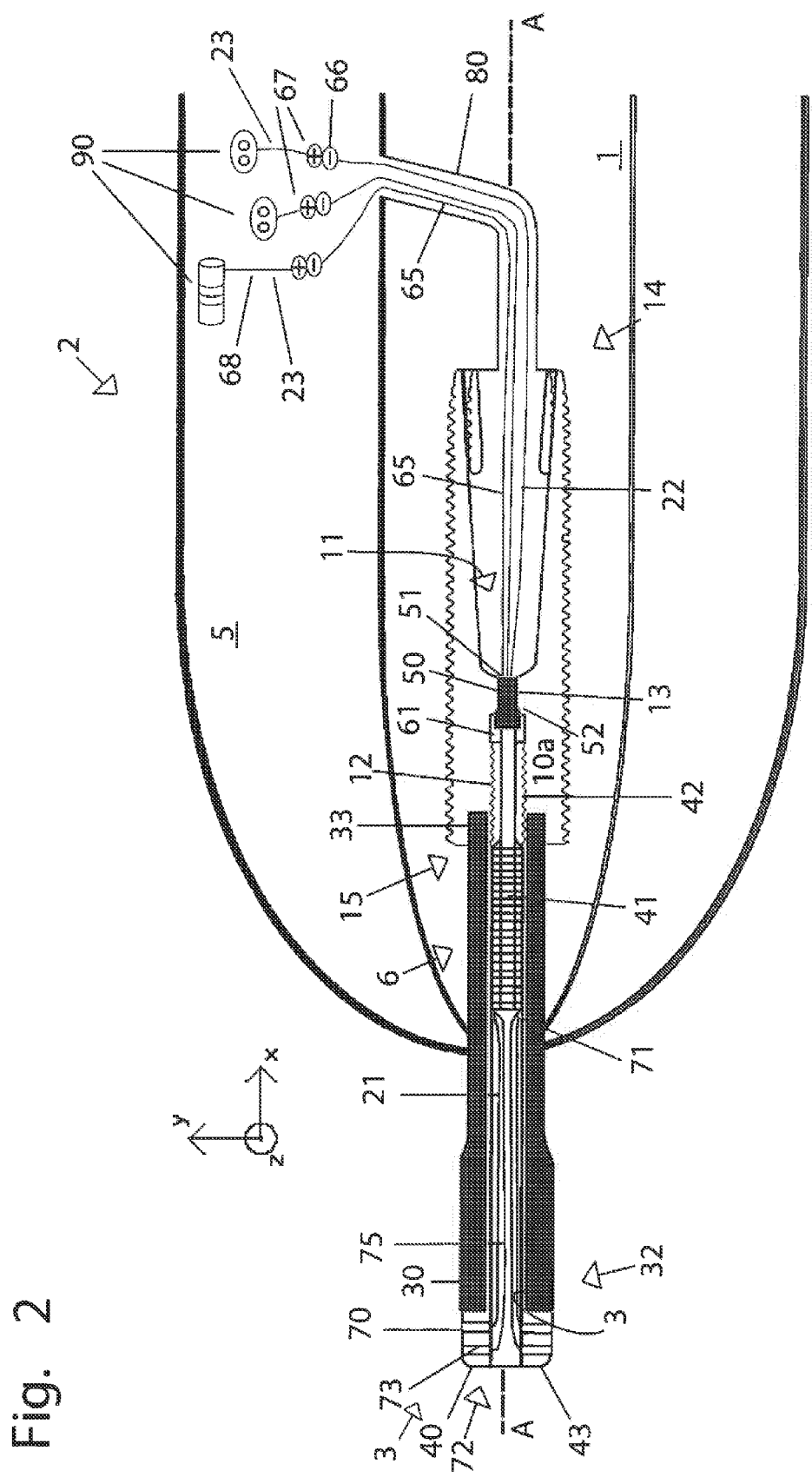
FIG. 2 shows a cross section of a fixing system as a part of the percutaneous gateway being implanted in a bone of a limb in an x-y plane according to a first embodiment.

The first exemplary embodiment of the present disclosure is schematically shown in FIG. 2. Here, an assembled fixing system as part of the percutaneous gateway for a bone anchored robotic prosthesis is shown after being implanted in a bone 1 of a limb (stump) 2. The fixing system comprises a fixture 10a, an abutment 30, an abutment fixing device 40, a sealing device 50 and a signal transmitting device 20.

Figure 3:
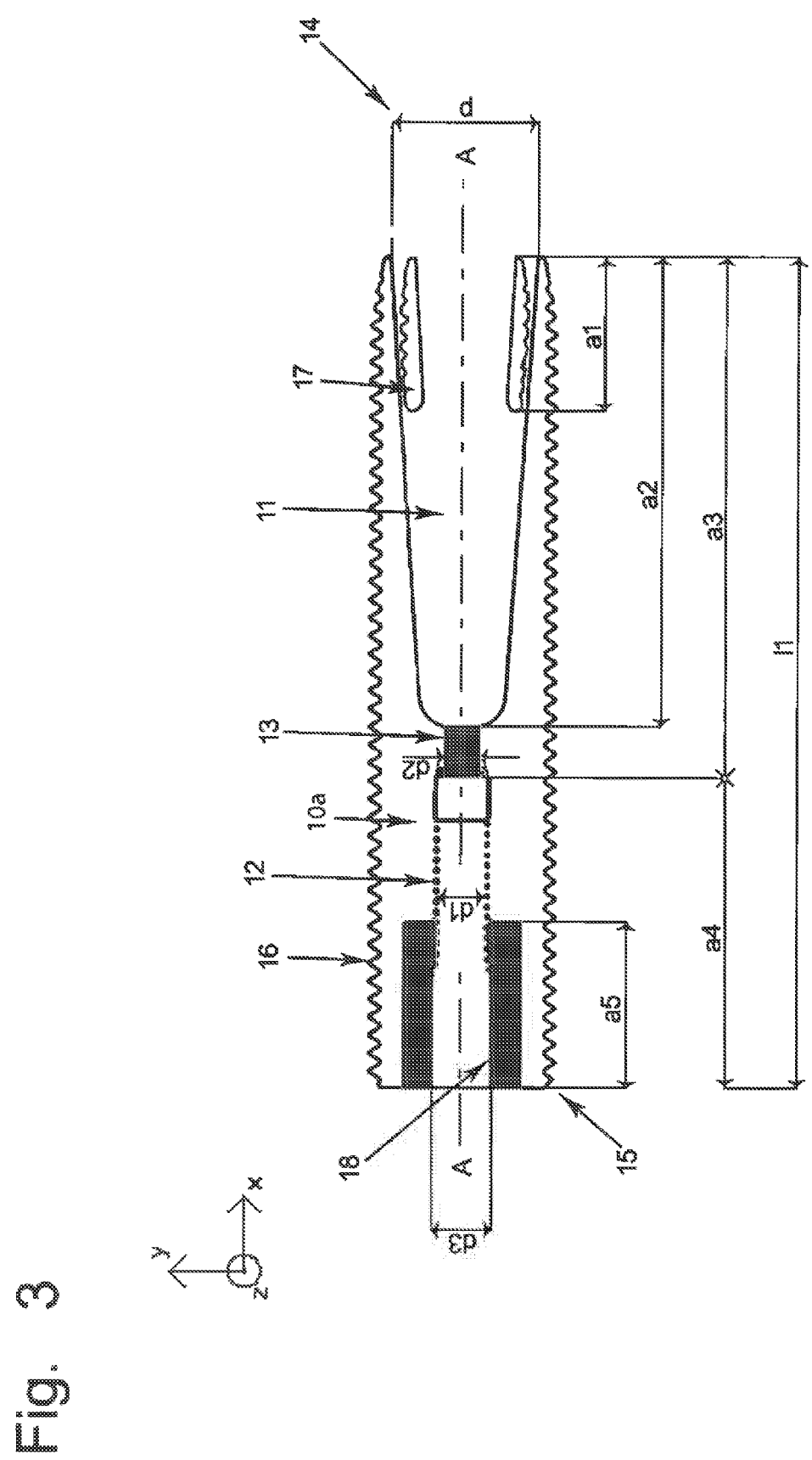
FIG. 3 is a cross section of a fixture used in the fixing system in the x-y plane according to the first embodiment.

A cross section of the fixture 10a according to the first embodiment is shown in FIG. 3. The fixture 10a is used as an anchoring element for a robotic prosthesis on the bone 1. Accordingly, the fixture 10a is, for example, surgically inserted into the bone 1 of an amputation stump of the limb 2. The design of the fixture 10a allows bone cells to grow tight around it (osseointegration) such that the fixture is long-term fixed in the bone 1. As explained below, the abutment 30 which serves, for example, as the fixing terminal for the robotic prosthesis outside the limb 2 is fixed to the bone 1 via the fixture 10a. The fixture 10a may be partly implanted with an inner section inside the bone 1. Preferably, according to the first embodiment, the fixture 10a is completely implanted inside the bone 1. Therefore, the whole fixture may be regarded as an inner section. Furthermore, the fixture comprises a through-hole 11 having an inner end 14 opening into the bone and an outer end 15 in the opposite direction with respect to a longitudinal axis A of the through-hole 11 and/or the fixture 10a. The outer end 15 may be directed to a drill 6 in the bone 1 through which the fixture 10a has been inserted from outside into the bone 1.

Figure 4:
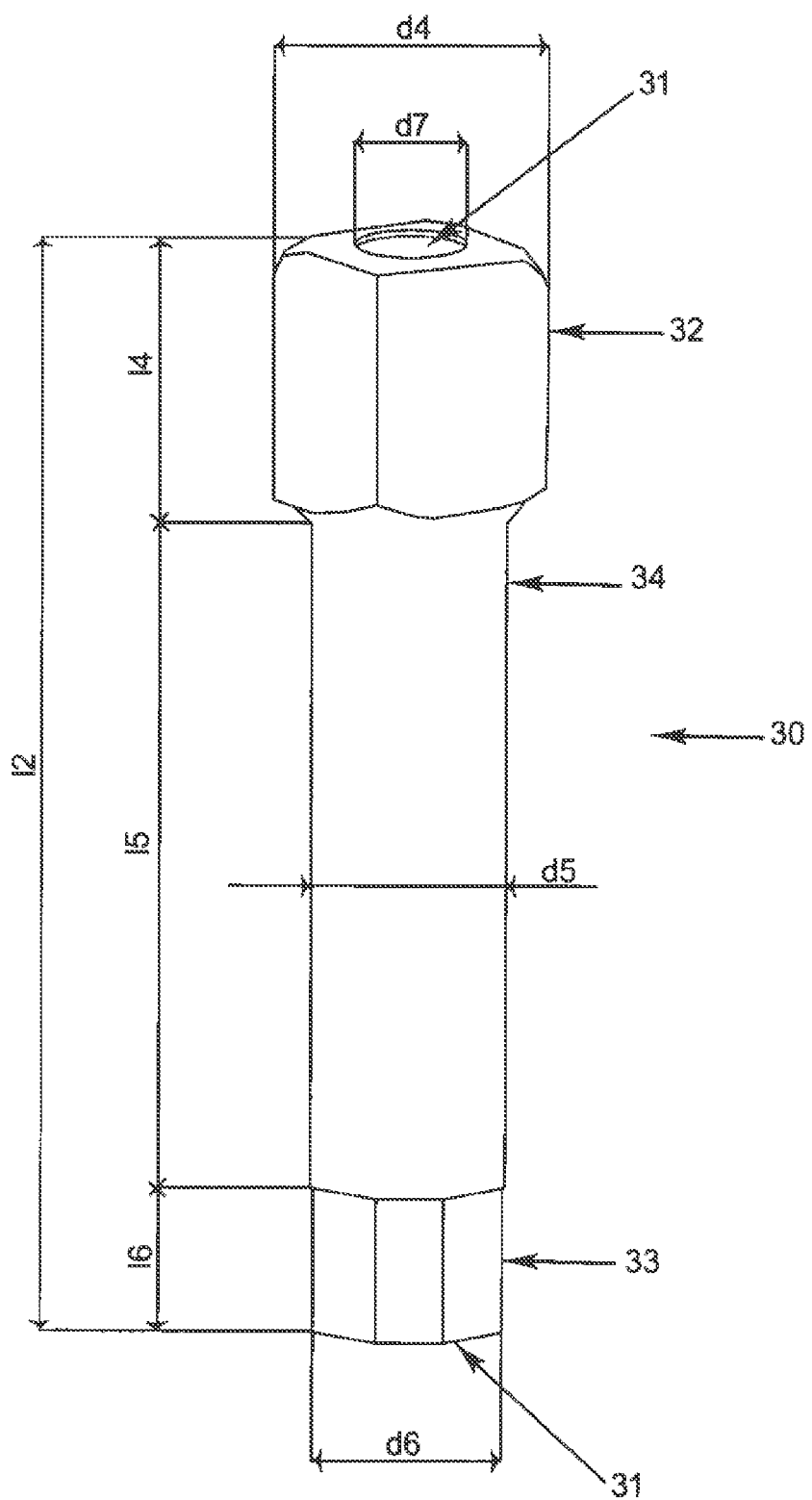
FIG. 4 is a perspective view in the z-direction of an abutment used in the fixing system according to the first embodiment.

A perspective view of the abutment 30 according to the first embodiment is shown in FIG. 4. The abutment 30 is partly inserted into the outer end 15 of the through-hole 11 of fixture 10a and partly exiting the stump 2 (and the bone 1). Accordingly, the abutment 30 may constitute a percutaneous passage. A head 32 of the abutment 30 may serve as a fixing terminal for the robotic prosthesis or other outside devices 91. The head 32 constitutes the outer end of the abutment 30. Furthermore, the abutment may comprise a fitting at the inner end opposite to the outer end. The fitting is adapted to be inserted into the fixture 10a. Preferably, the fitting is a hexagonal fitting 33.

Figure 5:
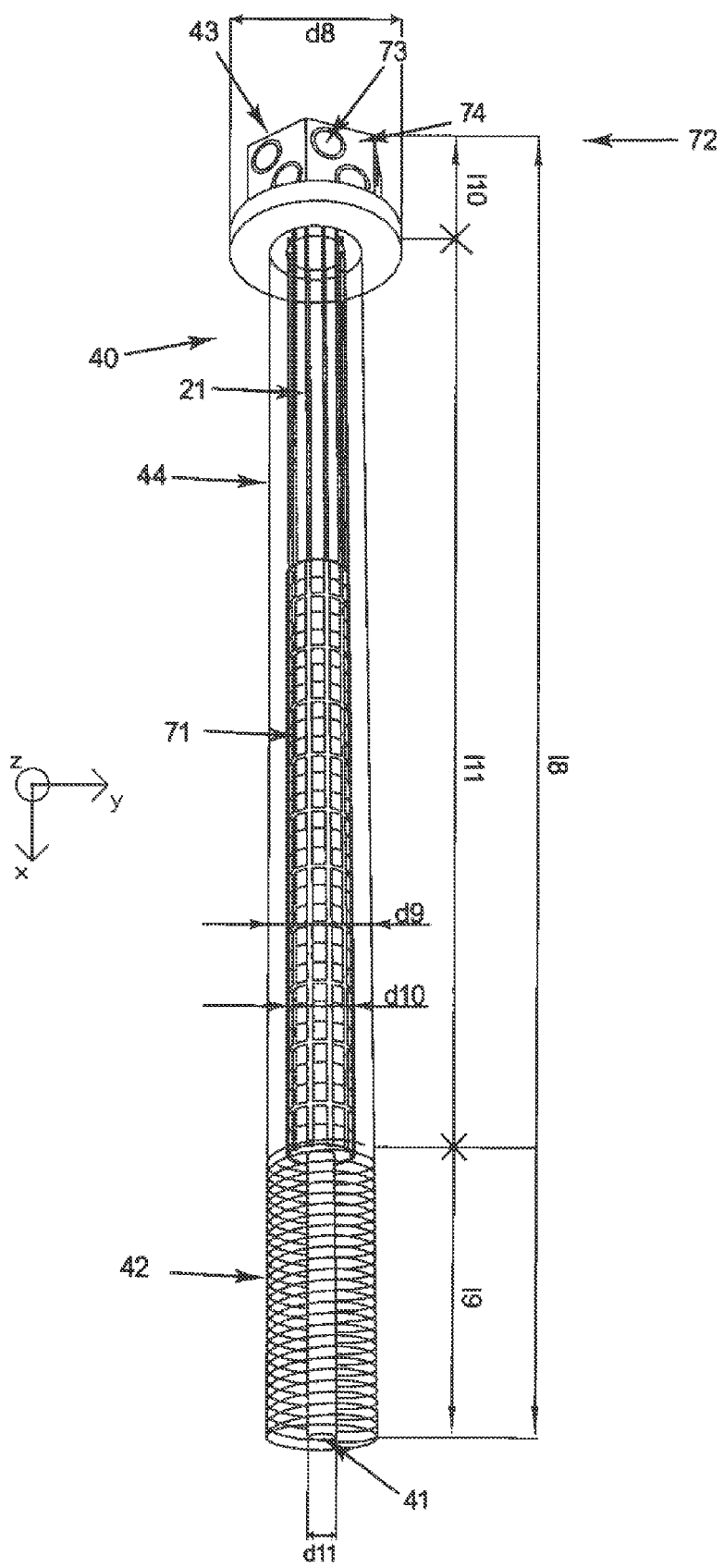
FIG. 5 is a perspective partially cutaway view in the z-direction of an abutment fixing device according to the first embodiment.

A perspective view of the abutment fixing device 40 according to the first embodiment is shown in FIG. 5. The abutment fixing device 40 is preferably a longitudinal screw which will be referred to as the abutment screw 40 in the following. The abutment screw 40 preferably goes through a (third) through-hole 31 of the abutment 30 and attaches the abutment 30 to the fixture 10a. An outer end 3 of the third through-hole 31 conforms to the head 32. That means, a head 43 of the abutment screw 40 is preferably pressed against the abutment 30 when the abutment screw 40 is being screwed into a first fixing section of the fixture 10a. The first fixing section of the fixture 10a is preferably an inner thread 12. Furthermore, the abutment screw preferably comprises a (fourth) through-hole 41.

Furthermore, the through-hole 11 of the fixture 10a is preferably closed and sealed by the sealing device 50. Accordingly, body fluid on the bone-side of the fixture 10a is prevented from exiting through the fixing system (percutaneous gateway) and bacteria are prevented from entering into the bone 1. Preferably, the sealing device 50 is a screw which will be referred to as the sealing screw 50 in the following. The sealing screw 50 preferably comprises a (second) through-hole 51 wherein a signal transmission device is fixed.

The signal transmitting device 20 is provided for transmitting, e.g. myoelectric signals from implanted electrodes 90 to the robotic artificial limb prosthesis through the fixing system or to transmit, for example, signals and/or power supply from the outside devices 91 to electric circuits inside the body as, for example, amplifiers which are housed in the electrode housings. For providing a long-term stable connection between the electrodes 90 and the robotic prosthesis, the signal transmitting device 20 is preferably fed through the implant through-hole which is constituted by the through-holes 11, 51, 41, 31 of the fixture 10a, the sealing screw 50, the abutment screw 40 and thereby also of the abutment 30. From the bone-side inner end 14 of the through-hole 11 of the fixture 10a, the signal transmitting device 20 is preferably guided through a drilled through-hole 80 running inside the bone 1 from the inner end 14 of the fixture 10a to the outside surface of the bone 1. The outside surface of the bone 1 is enclosed by a soft tissue 5 of the limb 2. Accordingly, the transmitting device 20 may be connected to the electrodes 90 and/or biosensors (not shown) and/or devices (not shown) inside the soft tissue 5.

In view of the best possibilities for assembling and repairing the percutaneous gateway including the fixing system, the transmitting device 20 is preferably divided into several transmitting parts 21, 22, and 23. A first signal transmitting part 21 is preferably located inside the abutment screw 40 and, according to the first exemplary embodiment, electrically connected to a second signal transmitting part 22 extending from the first transmitting part 21 through the sealing screw 50 inside the fixture 10a to the electrodes 90. Additionally, the electrodes 90 may be preferably connected to the second signal transmitting part 22 by a third signal transmitting part 23.

The above signal transmitting parts 21, 22, 23 are preferably connected by different connectors which will be explained later. Furthermore, on the other, i.e. the outer end of the signal transmitting parts 21, 22, 23 which are connected to each other, a further signal transmitting part is preferably connected to the first signal transmitting part 21 for transmitting signals to an amplifier or control circuit (not shown) for controlling the robotic prosthesis.

The respective through-holes may be understood as central openings, channels, through-openings, passages and so on. The term "signal transmission" may be understood as, for example, electric signal transmission, light signal transmission and so on, but also includes a power supply transmission. Furthermore, also a fluid may be transmitted via the signal transmitting device.

Detailed Description of the Respective Elements

In the following, the different elements of the percutaneous gateway including the fixing system are described in detail with reference to the respective drawings.

Fixture

The fixture 10a is shown in FIGS. 2 and 3. According to the first embodiment, the fixture 10a is preferably an essentially rotationally symmetric member extending in a longitudinal direction x over an overall length 11. As shown in FIG. 2, the fixture 10a preferably has a cylindrical shape and a longitudinal axis A extending in the x-direction. Furthermore, the fixture 10a may have the through-hole 11 (first through-hole) extending preferably from an inner end 14 which opens into the bone 1 to an outer end 15 opposite to the inner end 14 with respect to the longitudinal axis. The through-hole 11 preferably comprises a fixing portion having a first fixing section as a first female thread 12 for fixing the abutment screw 40 (abutment fixing device) and a second fixing section as a second female thread 13 for fixing the sealing screw 50 (sealing device). Furthermore, the through-hole 11 has such a shape that the second transmitting part 22 may be guided from the inner end 14 to the outer end 15.

The through-hole can also exit to the bone in any other direction than x, such as in the y-direction shown in FIG. 1. The fixture may have embedded the feedthrough connector 50 instead of a removable screw 50.

Preferably, the through-hole 11 runs in the longitudinal direction x over the entire first length 11 through the entire fixture 10a. The inner end of the fixture 10a, which is preferably to be inserted into the bone 1 at first, is preferably identical to the inner end 14 of the through-hole 11. The same applies for the outer end 15 of the fixture 10a. The outer surface area of the fixture 10a is preferably completely, but at least partly, provided with a male thread 16.

The through-hole 11 of the fixture 10a is, for example, divided into five sections over the overall length 11 beginning from the inner end 14. The first section is, for example, arranged within a first distance a1 from the inner end 14 with respect to the longitudinal direction x. In the first section, the cylindrical body of the fixture 10 may be slotted. That means, there are, for example, four slits 16 extending from the inner end 14 of the fixture 10a in the longitudinal direction x over the first distance a1. Preferably, the slits 16 have a spiral form. Furthermore, nuts with small bores may be provided instead of slits. The slits (nuts) will help the bone cells to grow tight around the fixture 10a (osseointegration). Furthermore, the process of inserting the fixture into the bone may be improved because the fixture 10a itself is used for drilling into the bone 1.

A second section is, for example, arranged adjacent to the first section with respect to the longitudinal direction x (i.e. proximate in a direction to the outside of the body). In the second section, the inside diameter of the through-hole 11 decreases from an inner end inside diameter d to a second diameter d2 of a second female thread 13 (second fixing section). The second female thread 13 preferably constitutes a third section which is preferably located adjacent to the second section in the longitudinal direction x. Accordingly, in the second section, the wall thickness of the fixture 10a increases with respect to the longitudinal direction x up to the maximum value which is preferably achieved in the third section. The second section ends at a distance a2 in the longitudinal direction x from the inner end 14 of the fixture 10a. The second transmitting part 22 is preferably partly housed in the first and second section.

The third section starts at the distance a2 in the longitudinal direction x from the inner end 14 and extends to a distance a3 in the longitudinal direction x from the inner end 14. In the third section, the through-hole 11 preferably comprises the second female thread 13. Furthermore, the sealing screw 50, which will be described below, is adapted to close and seal the inner hole 11 of the fixture 10a by being screwed into the second female thread 13 of the fixture 10a.

In the fourth section, which is provided adjacent to the third section, a first female thread 12 (first fixing section) with a first diameter d1 is at least partly formed. The unthreaded portion of the fourth section has preferably the same first diameter d1. The fourth section extends from a distance a4 from the outer end 15 of the through-hole 11 to a distance a5 from the outer end 15 with respect to the longitudinal direction x. Preferably, the first female thread 12 starts with a distance of, for example, about 4 mm (dependent on the shape of the sealing screw 50) with respect to the third section. Accordingly, a sealing screw head 53, which will be explained later, does preferably not come into contact with the abutment screw 70, when the sealing screw 50 is screwed into the second female thread 13.

Preferably, the sum of distances a3 and a4 corresponds to the overall length 11 of the fixture 10a and the through-hole 11. The abutment screw 40 is adapted to be fixed in the third section of the fixture. That means, the abutment screw 40 is preferably adapted to be screwed into the first female thread 12. Therefore, the abutment screw 40 preferably comprises a male thread 42 having a corresponding size.

A fifth section extends over a length a5 from the outer end 15 of the through-hole 11 in the longitudinal direction x. The fifth section is preferably provided to receive the abutment 30 therein. The interior surface of the fifth section is formed as, for example a hexagonal female fitting 18 having a third inside diameter d3 and corresponding to the inner end 33 of the abutment 30.

Diameter d3 is preferably larger than diameter d1, and diameter d1 is preferably larger than diameter d2, and diameter d is preferably larger than diameter d2.

The fixture is preferably made of biocompatible, long-term implantable material, for example of titanium. The fixture allows a reliable and long-term stable fixation of the whole fixing system in the bone 1. The fixture may be also used in bone anchored prosthesis having no robotic function.

Abutment

Next, the abutment 30 will be described referring to FIGS. 2 and 4. The abutment 30 is a preferably rotationally symmetric member extending with a length 12 into the longitudinal direction x. The abutment 30 has preferably a cylindrical shape with a central through-hole 31 (third through-hole) extending in the longitudinal direction x with the same length 12 between the abutment screw head 32 as the outer end and hexagonal male fitting 33 as the inner end. The central through-hole 31 may have a constant diameter d7 and may be adapted to house the abutment screw 40 therein.

The abutment 30 is preferably divided in, for example, three sections. The first section is constituted by the abutment screw head 32 having a quadratic form, for example, and an outside diameter d4 and a length 14 in the longitudinal direction x. The second section is the shaft section 34 having an outside diameter d5 and a length 15. The third section is located opposite to the first section with respect to the longitudinal direction x and constitutes the inner end of the abutment 30. The inner end of the abutment 30 is preferably formed as a hexagonal male fitting 33. The hexagonal male fitting 33 has an outside diameter d6 and a length 16 in the longitudinal direction x. The hexagonal fitting 33 allows the abutment 30 to be fitted in the hexagonal female fitting 18 of the fixture 10a without deformation. However, the hexagonal male fitting 33 and the hexagonal female fitting 18 of the fixture 10a may be replaced by, for example a conical fitting.

Furthermore, the abutment 30 has to provide a comfortable skin penetration area. For these reasons the obvious cross section shape of the shaft 34, normal to its axis, is preferably circular.

Furthermore, the abutment shaft 34 should direct the fracture point due to overload or fracture, in particular, because the fixture 10a should be protected from overload. Therefore, it is desirable that the fracture occurs as far outside the limb as possible, as a surgical need to firmly grip the residual shaft when replacing the abutment. If a fracture point is near to the skin penetration area or even inside the stump, the procedure might require surgical incision which is normally not required when replacing an abutment. Accordingly, it is preferred that the abutment 30 has a design with a predetermined braking point being as far as possible outside the limb 2.

The abutment 30 is preferably made of biocompatible, long-term implantable material, for example of titanium.

Abutment Fixing Device

Figure 6:
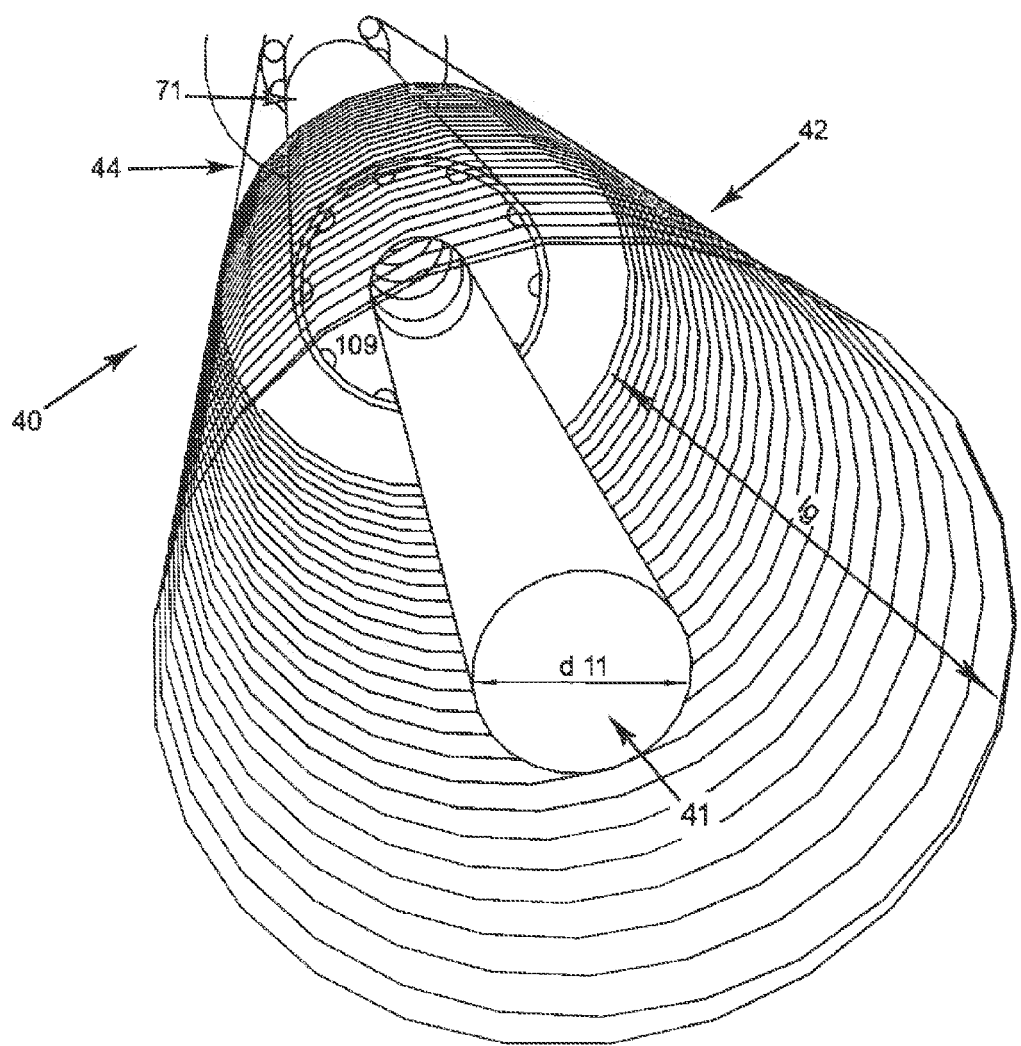
FIG. 6 is a perspective partially cutaway view of the bottom of the abutment fixing device according to the first embodiment

Next, the abutment screw 40 will be described with reference to FIGS. 2, 5 and 6. The abutment 30 is adapted to be fixed in the fixture 10a by the abutment screw 40. The abutment screw 40 is a longitudinal screw having an overall length 18. The abutment screw 40 comprises a male thread 42 on its inner end portion over a distance 19 in the longitudinal direction x. The male thread 42 of the abutment screw 40 is adapted to fit into the first female thread 12 of the fixture 10a (see above).

Furthermore, the abutment screw 40 comprises a screw head 43 which is adapted to be engaged by a tool for screwing-in and -out the abutment screw 40, and for contacting, for example, the abutment head 32, and thereby pressing the abutment 30 into the fitting 18 in the fixture 10a. The abutment screw head 43 has a length 110 and a maximum diameter d8.

A preferably un-threaded shaft 44 of the abutment screw 40 has an eleventh length 111 and a ninth diameter d9. Furthermore, the abutment screw 40 comprises a preferably central through-hole 41 (fourth through-hole) having an inside diameter d10 inside the screw shaft 44 and the screw head 43, and an inside diameter d11 inside the thread 42. Preferably, d11 is smaller than d10.

The portion of the through-hole 41 having the larger inside diameter d10 is preferably adapted to house, at least partly, the first transmitting part 21. The portion of the through-hole 41 having the smaller eleventh inside diameter d11, is preferably the portion wherein a part of the second transmitting part 22 is fed through.

In view of the above inside diameters, the wall-thickness of the abutment shaft 40 is increased inside the threaded portion 42. Therefore, the abutment screw 40 can be loaded with a higher torque force during insertion.

The abutment screw 40 is preferably made of biocompatible, long-term implantable material, for example of titanium.

First Transmitting Part of the Transmitting Device

The abutment screw 40 preferably houses the first signal transmitting part 21, as shown in FIGS. 2, 5, 6 and 23. Preferably, the first signal transmitting part 21 is embedded in the abutment screw 40.

The first signal transmitting part 21 may comprise a first connector 71 being preferably located inside the abutment screw shaft 44. Preferably, the first connector 71 is arranged inside the portion of the through-hole 41 having the larger diameter d10. According to the first embodiment, the first connector 71 is preferably an in-line female connector.

The term "in-line" means that different contacts of a connector are arranged on a common axis, and therefore on or in a line.

Figure 7:
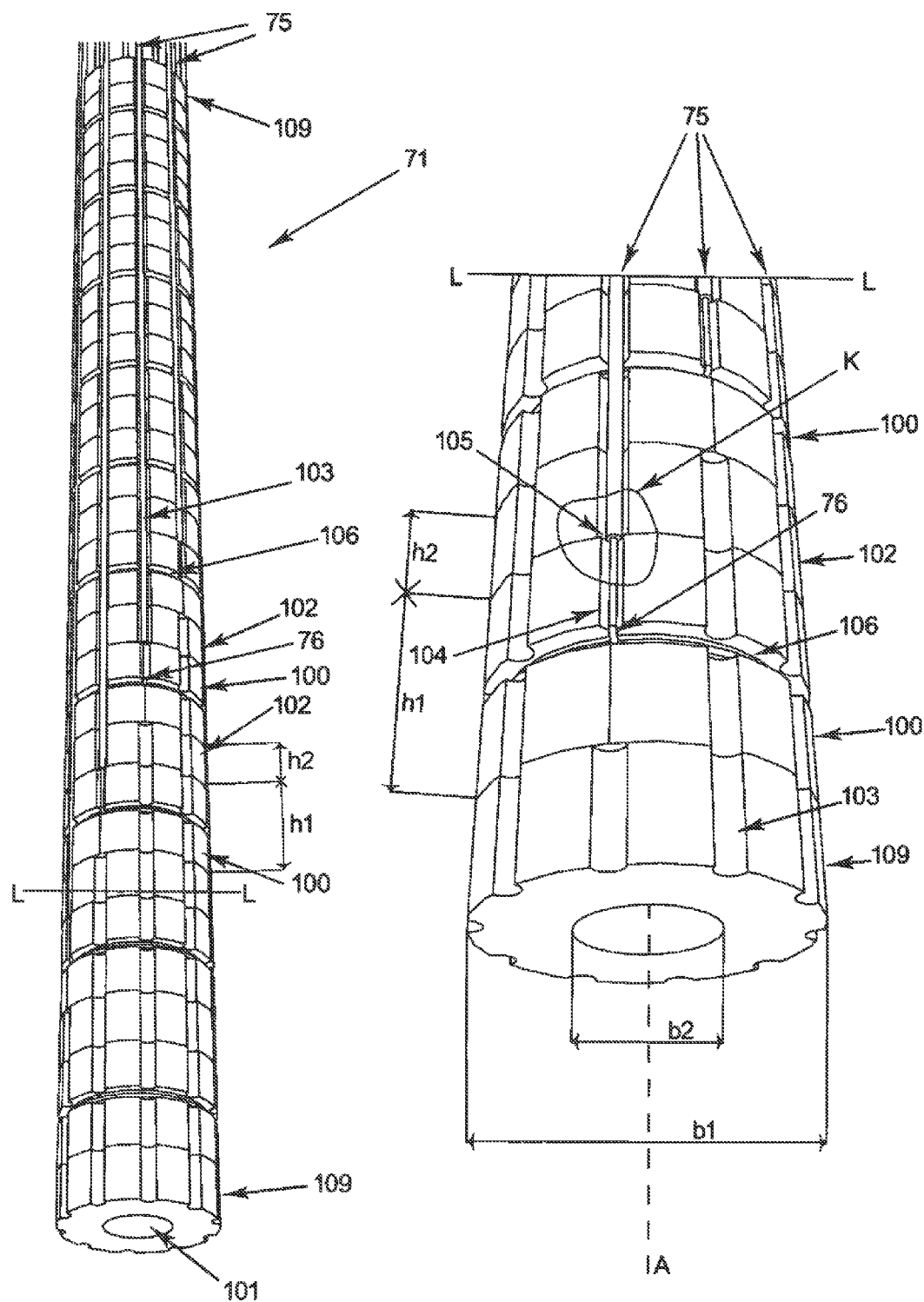
FIG. 7 is a perspective view in a) and a detailed perspective view of the lower end in FIG. 7a) in b) of a first female connector adapted to be inserted in the abutment screw of FIG. 4 according to the first embodiment.
Figure 23:
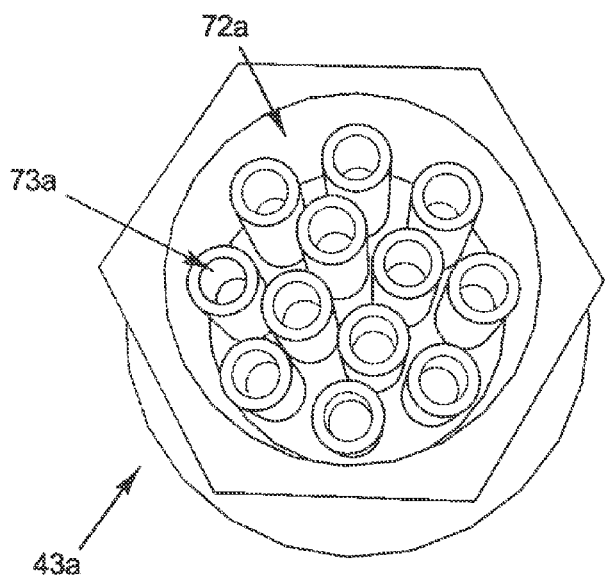
FIG. 23 shows a perspective view of an abutment fixing device head according to a second embodiment.

On the other side, the first signal transmitting part 21 preferably has a head connector 72 in the abutment screw head 43 (third connector). The head connector 72 in the screw head 43 is, for example, a side-contact connector, wherein different contacts 73 are provided in the side walls 74 of the screw head 43. The different contacts 73 may be connected to transmitting means in form of insulated cables 75 (see FIGS. 2 and 7) by crimping or welding. The cables 75 are preferably fed through the through-hole 41 to the first in-line connector 71, respectively. The head connector can also have the contacts arrange in a parallel way such as shown in FIG. 23.

Figure 8:
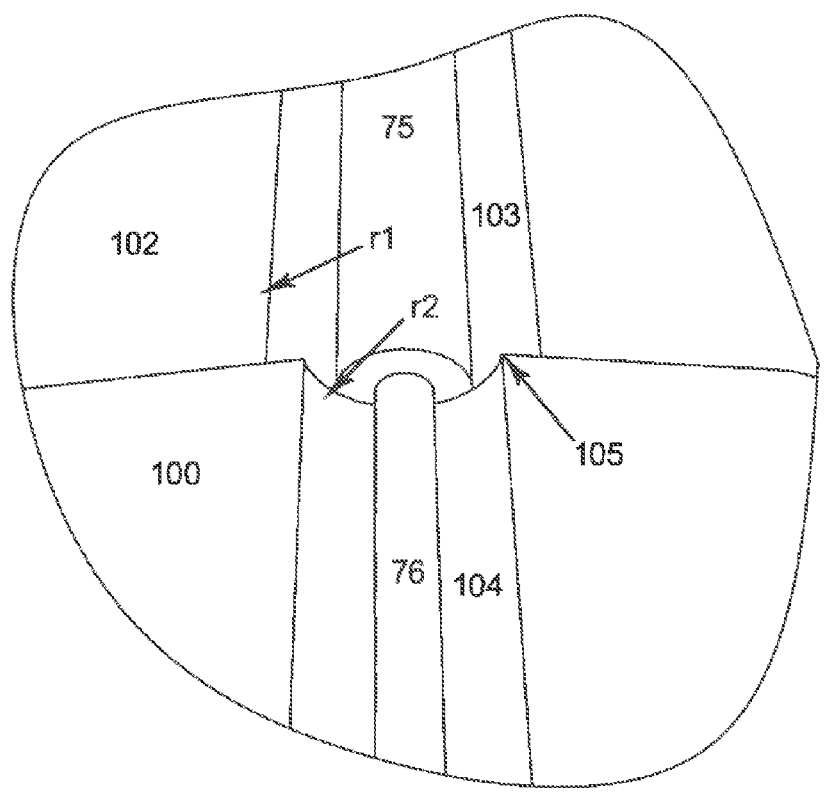
FIG. 8 is a detailed perspective view of a detail "K" of FIG. 7 of a longitudinal groove formed for a transmitting means provided on the outer surface of the female connector according to the first embodiment.

The first in-line female connector 71 is preferably configured by contact sockets (female contacts) 100 and female insulating means (insulating sockets) 102, as shown in FIGS. 7a) and b) and FIG. 8. FIG. 7b) shows a detailed view of the first in-line female connector 71 below the line L-L in FIG. 7a). Each female contact socket 100 and each female insulating means 102 has a preferably cylindrical shape with a through-hole 101 wherein an in-line male connector 61 (second connector) may be inserted (plugged). Each contact socket 100 has a height h1, an outside diameter b1 and an inside diameter b2. Each female insulating means 102 has a height h2, and preferably the same outside diameter b1 and inside diameter b2.

The first in-line female connector 71 is preferably configured by arranging the contact sockets 100 in-line on the longitudinal axis A together with the female insulating means 102. For insulating each contact socket 100 from the proximate contact socket 100, preferably one female insulating means 102 is arranged between each couple of contact sockets 100.

The contact socket 100 and the female insulating means 102 are fixed on each other by, for example, a medical adhesive. Furthermore, it is also advantageous, if one side, for example, the outer end (directed to the outside of the body) with respect to the longitudinal direction x of each contact socket 100 and of each female insulating means 102 has a recess, respectively, and the inner end with respect to the longitudinal direction x of each contact socket 100 and of each female insulating means 102 has a corresponding projection, respectively, which fit together when they are coupled. The only modification of the ultimate insulating means 109 is the flat termination in one of it ends.

The number of the contact sockets 100 depends on the required number of signals to be transmitted. In the present embodiment, ten contact sockets 100 are preferred. Furthermore, it is preferred that both ends of the first female connector 71 are insulated. Accordingly, at least 11 female insulating means 102 may be necessary. Accordingly, a connector stack is configured by an in-line arrangement of the different contact sockets 100.

A sleeve (not shown) made of metal wire is arranged in each contact socket 100. The shape of the contact sleeve is formed by wires strung at an angle to the socket's axis (not shown). When a male pin contact element 110 is inserted into the corresponding sleeve of the contact socket 100, the wire may stretch around it thereby providing a number of linear contact paths. Therefore, an electrical connection between the male pin contact element 110 and the contact socket 100.

Figure 9:
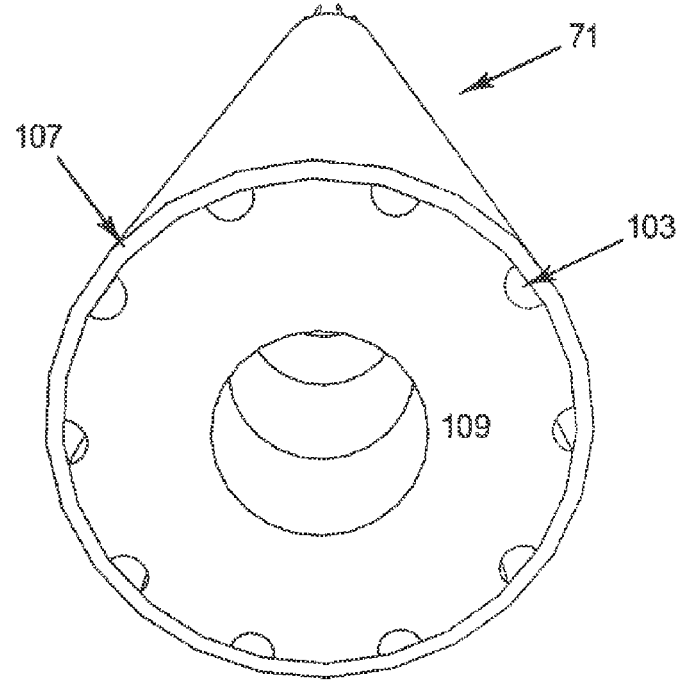
FIG. 9 is a detailed perspective view of the bottom of the first female connector according to the first embodiment.

Furthermore, each contact socket 100 has to be connected to the corresponding insulated cable 75 from the abutment screw head connector 72, as stated above. In order to safe space and preserve a flat outside surface around the first female connector 71, a longitudinal groove 103 is formed in the surface of the first female connector 71 parallel to the axis A for each insulated cable 75, respectively. Each groove 103 has a first radius r1 and the radius is dimensioned for accommodating the insulated cable 75 such that the outside diameter of the first female connector 71 is not increased because of the inserted cable 75 (see FIGS. 7 to 9).

The electrical connection between the respective cable 75 and the corresponding contact socket 100 is preferably ensured by a bared end portion 76 of each cable 75 starting at the border 105 between an insulating means 102 and the proximate contact socket 100. The bared end portion 76 has a smaller diameter than the insulated cable 75. Accordingly, a groove 104 extending in the longitudinal direction x on the surface of the contact socket 100 which is to be connected to the bared end portion 76 has preferably a second radius r2 being smaller than the first radius r1, as shown in FIG. 8. Therefore, the cable 75 and, in particular, its core assembly (that is, the bared end portion 76) may be guided in a straight line, in particular, at the intersection between the bared end portion 76 and the insulated part of the cable 75 (see FIG. 8).

Furthermore, each contact socket 100 may have an annular groove 106 having preferably the same second radius r2. The annular groove may be provided middle of the contact socket regarding the height direction (x-direction). The bared end portion 76 of the cable may also be guided through this annular groove 106. Furthermore, the electrical connection between the bared end portion 76 of the cable 75 and the respective contact socket 100 may be improved by 360 deg welding the bared end portion 76 to the surface of the annular groove 106.

Since this first in-line female connector 71 is preferably housed inside the abutment screw 40 which is preferably made from titanium, it requires insulation 107 between the respective contact sockets 100 and the housing (abutment screw 40). This is achieved by, for example, rolling silicon-sheets until reaching a wall thickness of, for example, 0.1 mm, as can be seen from FIG. 9.

The first in-line female connector 71 is preferably completely housed in the abutment screw 40. Accordingly, the first female connector 71 fits into the portion of the through-hole 41 having the inside diameter d10 inside the shaft 44.

The basic for the contact sockets 100 may be standard designed for medical use. Accordingly, the socket contacts are preferably made of bio-compatible materials. The female insulating means 102 are preferably made by PEEK or Silicon, and sealing between the each contact socket 100 and the respective insulating means 102 is provided by a long-term implantable adhesive, for example.

Sealing Device

Figure 10:
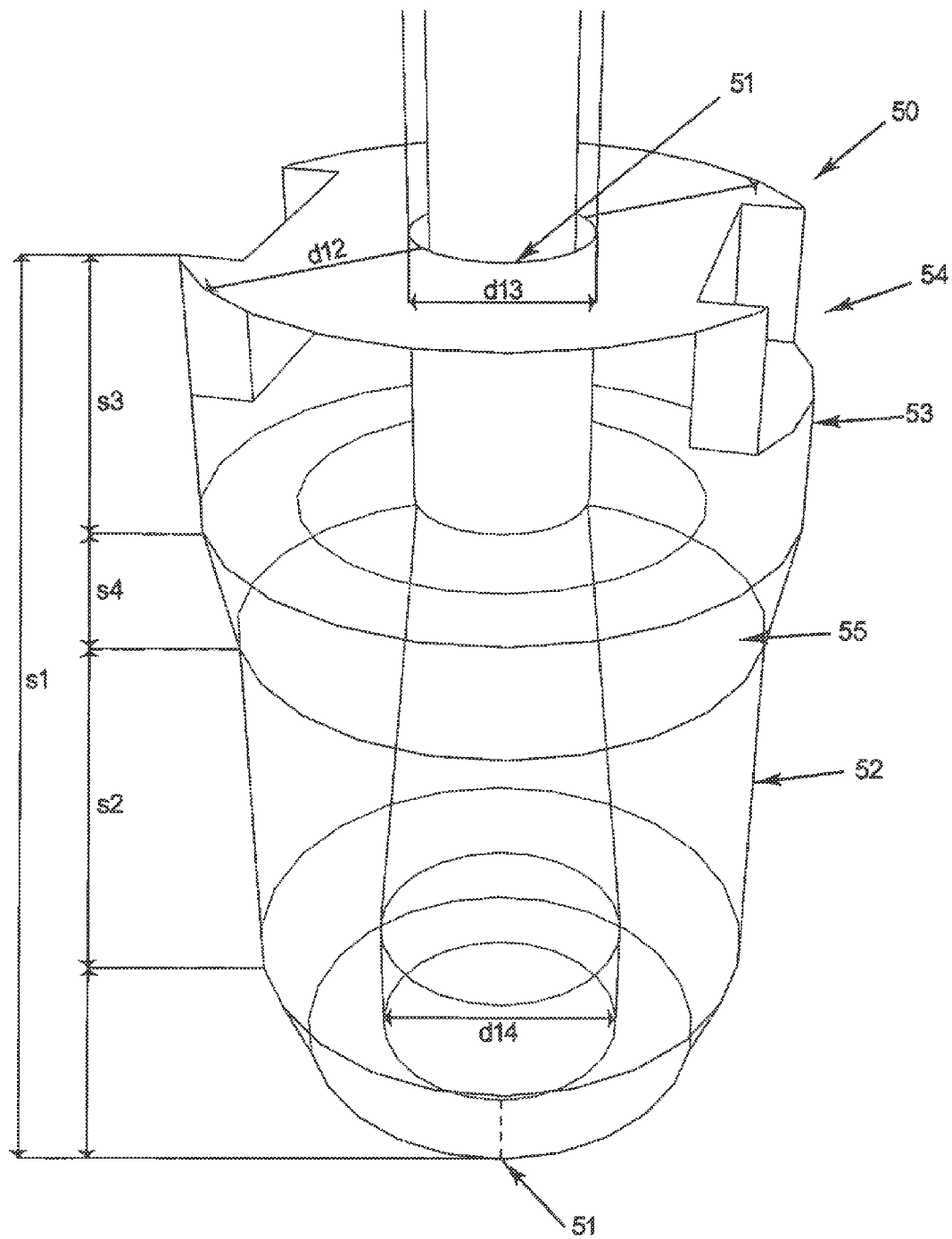
FIG. 10 is a partially cutaway perspective view of a sealing device according to the first embodiment.

The sealing screw 50, which is adapted to be screwed into the second female thread 13 of the fixture 10*a* and thereby sealing the outside surface of the sealing screw 50 to the inside surface the fixture 10*a*, is shown in FIG. 10. The sealing screw 50 has a male thread 52, for example, in form of a standard male. The sealing screw 50 has an overall length s1 in the longitudinal direction x. The male thread 52 has a length s2 in the longitudinal direction x. Furthermore, the sealing screw 50 comprises a head 53 having a length s3 in the longitudinal direction x and a diameter d12. The head 53 comprises one or more recesses 54 to be engaged by a tool for screwing the sealing screw in and out. Between the head 53 and the male thread 52 is a thread clearance 55. Accordingly, the head 53 and the male thread 52 are arranged with a distance s4 between.

The sealing screw 50 preferably has a through-hole 51 (second through-hole). The through-hole 51 of the sealing screw 50 has an inside diameter d13 in the screw head 53. Furthermore, inside the portion having the male thread 52, the inside diameter d12 of the through-hole 51 increases preferably conically to an inside diameter d14 at the inner end of the fourth throw hole 51 opposite to the screw head 53. That means, the fourth through-hole 51 preferably has a conical shape inside the threaded portion 52 of the sealing screw 50.

The sealing screw 50 is preferably made of biocompatible, long-term implantable material, for example of titanium.

Second Connector

Figure 11:
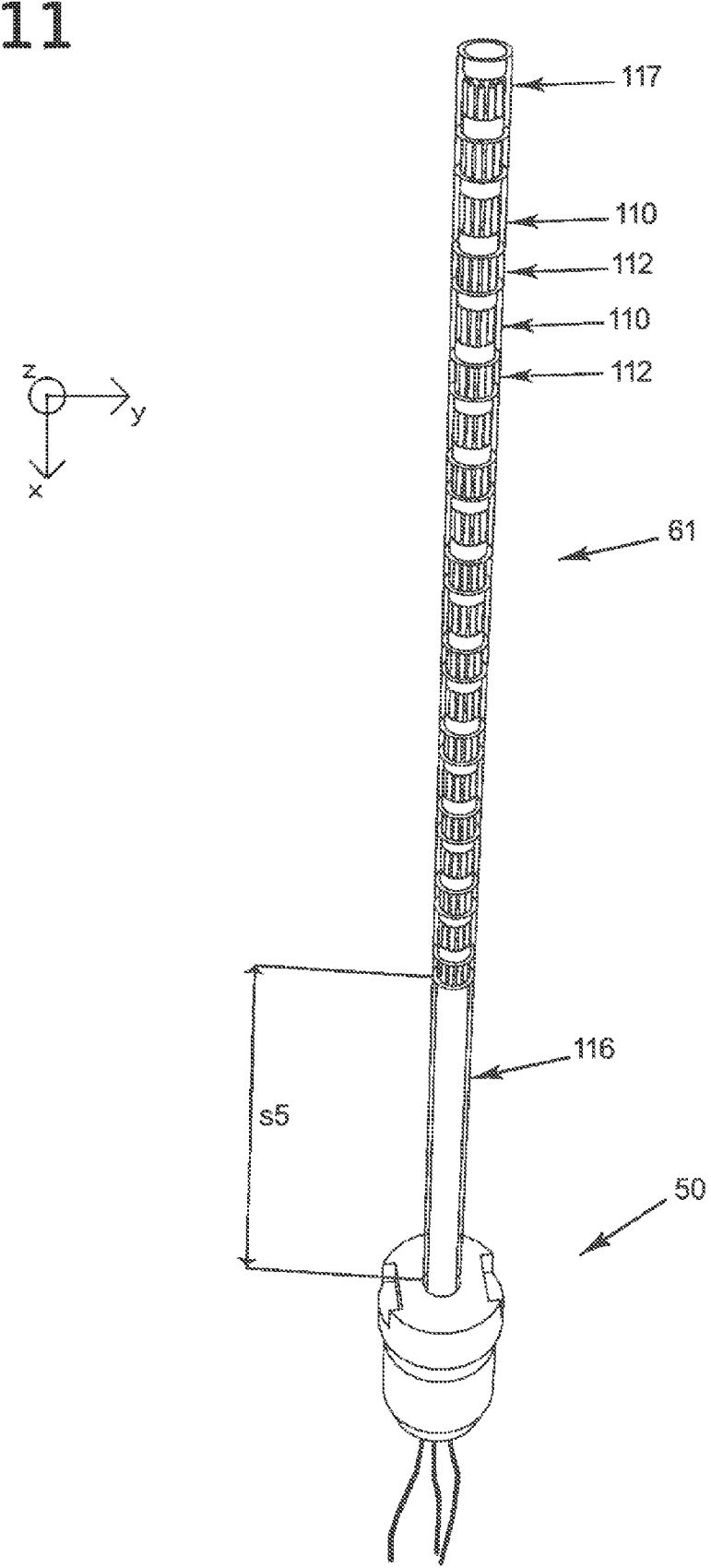
FIG. 11 is a partially cutaway perspective view of the sealing device comprising a first in-line male connector according to the first embodiment.

As shown in FIGS. 2 and 11, the first in-line male connector 61 (second connector) is preferably adapted to be fixed in the through-hole 51 of the sealing screw 50, in particular, inside the head 53 of the sealing screw 50 by, for example, a medical adhesive. The first in-line male connector 61 comprises male contact elements 110 and male insulating element 112 arranged in-line on a common axis A, wherein the insulating elements 112 are arranged as insulating means between the respective male contact elements 110 corresponding to the above described contact sockets 100 and female insulating means 112 (see FIG. 12). The male contact elements 110 and the insulating elements 112 are fixed on each other by a medical adhesive, for example, such that a connector pin is configured.

Furthermore, the inner and outer end of each male contact element 110 may have a recess, respectively (see FIG. 13*a*) and *b*)). Accordingly, the inner and outer end of each insulating element 112 may have a corresponding projection, respectively (see FIG. 14*a*) and *b*)). Therefore, the recess and the projection may fit together when the respective male contact elements 110 and insulating elements 112 are coupled.

Figure 12:
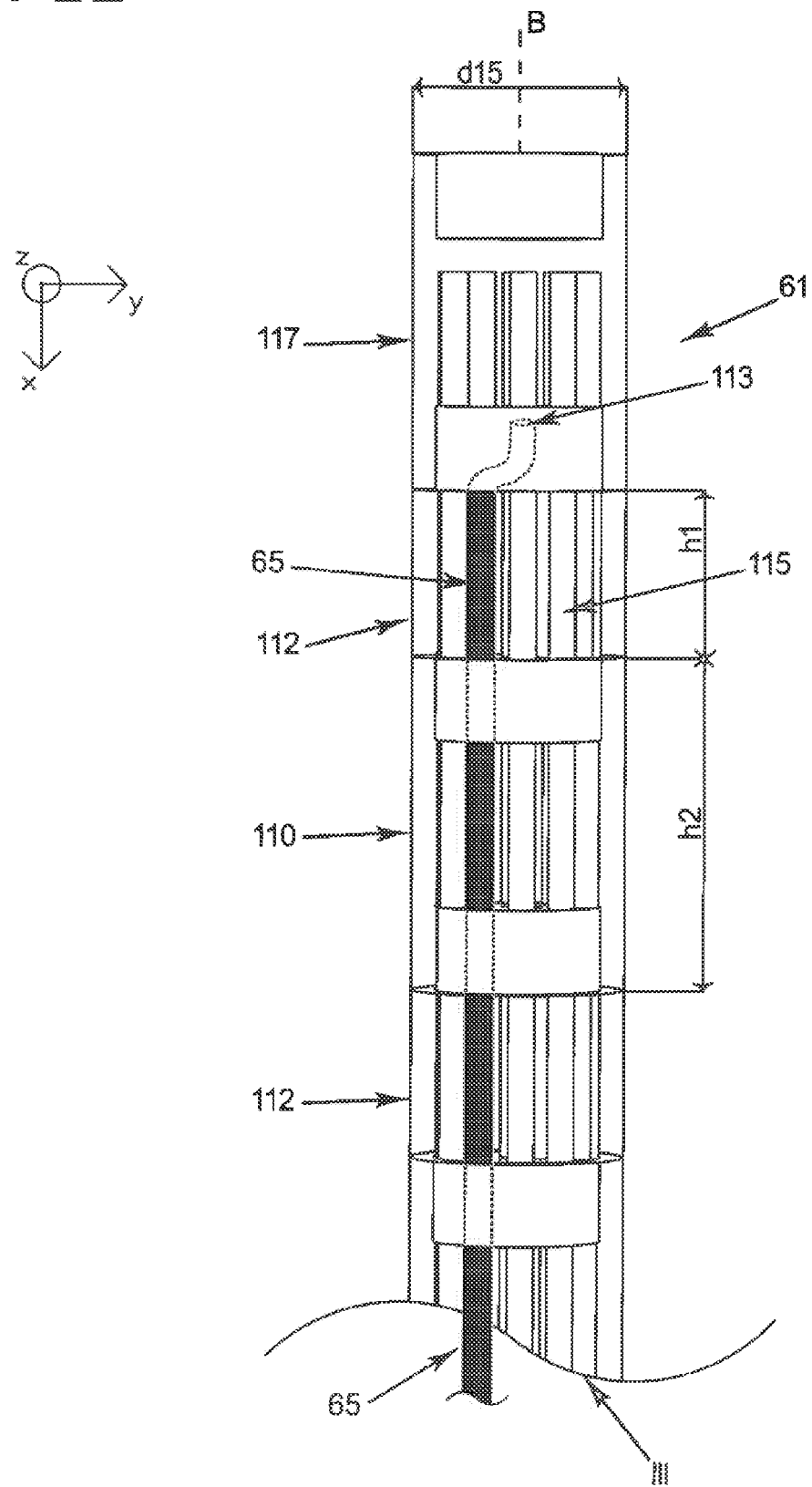
FIG. 12 is a detailed partially cutaway perspective view of an outer end portion the first in-line male connector according to the first embodiment.

The contact surface height and outside diameter of each male contact element 110 preferably corresponds to the height h1 and the inside diameter b2 of the corresponding contact socket 100 of the first in-line female connector 71, respectively (see FIG. 12). The height and diameter of each insulating element 112 preferably corresponds to the height h2 and inside diameter b2 of the corresponding female insulating means 112 of the first in-line female connector 71. Accordingly, the first in-line male connector 61 preferably has a maximum outside diameter d15 corresponding to the minimum inside diameter b2 of the corresponding through-hole 101 inside the contact socket 100 and insulating means 102. Furthermore, the number of male contact elements 110 preferably corresponds to the number of contact sockets 100. Accordingly, the in-line male connector 61 comprises in this embodiment ten male contact elements 110.

Figure 13:
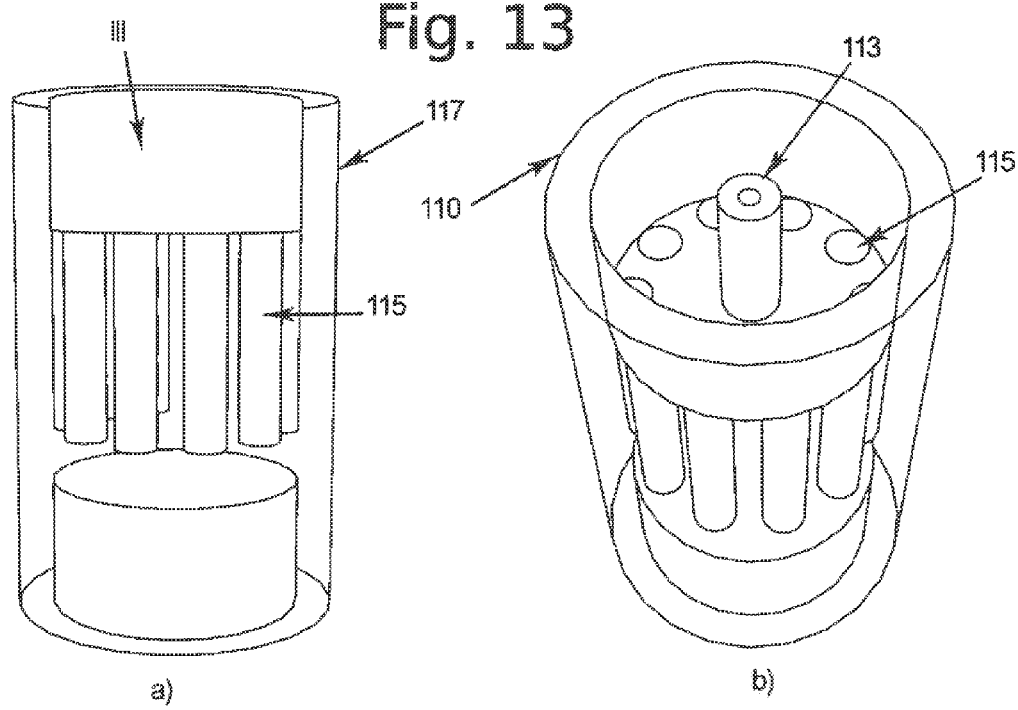
FIG. 13 is a partially cutaway perspective side view of an end male contact element in a) and angled partially cutaway perspective view from above from an intermediate male contact element in b) of the first in-line male connector according to the first embodiment.
Figure 14:
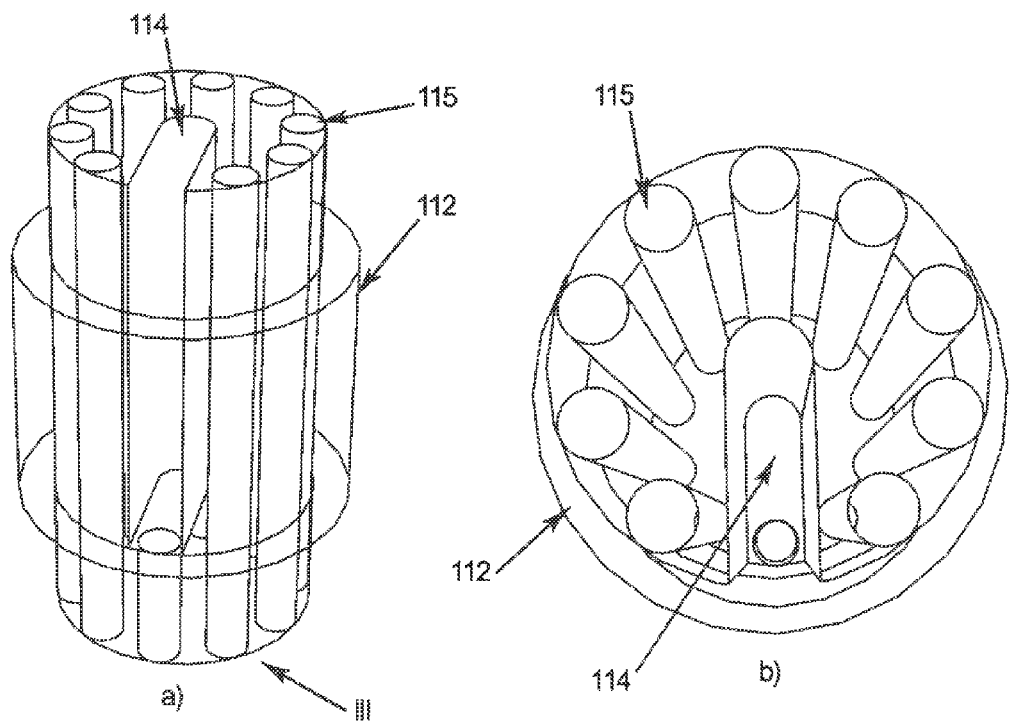
FIG. 14 is a partially cutaway perspective side view in a) and a partially cutaway bottom view in b) of an insulating element according to the first embodiment

Both, the male contact element 110 and the insulating element 112 of the first in-line male connector 61 comprise at least one through-hole 111 in the longitudinal direction x for guiding at least one cable 65 as part of the second transmitting part 22 through the sealing screw 50. Each male contact element 110 is connected to a respective cable 65 by crimping the cable 65 to a central crimping contact 113, for example, as shown in FIGS. 12 and 13b). The respective cable 65 is preferably guided through a U-shaped hole 114 of the proximate insulating element 112 to the corresponding through-hole 111, as schematically shown in FIGS. 12 and 14a) and b). It is preferred that each cable is guided in a separate cable channel 115. Therefore, in the present embodiment, the elements 110 and 112 comprise ten circularly arranged channels 115 instead of one through-hole 111, respectively. An exemplary course of one cable is shown in FIG. 12. Furthermore, the circular arranged channels 115 in an outermost (first) male contact element 117 are preferably closed for sealing the inside of the first male connector 71 from the outside, as shown in FIGS. 12 and 13a). Accordingly, body fluids and bacteria may be prevented from entering or exiting the in-line male connector 61.

The insulating elements 112 are preferably made from Silicon or PEEK. Furthermore, between the first insulating element 112 and the sealing screw 50, there is preferably a pin extension 116. The pin extension 116 is provided for bridging the distance from the sealing screw head 53 to the first female connector 71, i.e. for bridging the length of the male thread 42 of the abutment screw 40 plus the distance of the unthreaded portion in the fourth section of the fixture 10a adjacent to the sealing screw head 53 (see above). The pin extension has a length s5 in the longitudinal direction x and the same outside diameter ad the male elements 110, 112.

The cable 65 (second transmitting means) is preferably a shielded and insulated cable. That means, the core is coated by a first insulating layer and the insulating layer is coated by a shielding layer. Furthermore, the shielding layer is coated by a second insulating layer. The second insulating layer constitutes the outside surface of the shielded cable. Preferably, the shielding (shielding layer) of the cable 65 starts in the conical portion of the through-hole 51. Accordingly, when the diameter of the cable 65 is reduced because the shielding (shielding layer and second insulating layer) is omitted inside the head 53 of the sealing screw 50, the cable 65 fits optimal in the fourth through-hole 51 of the sealing screw (not shown). The shielding may be omitted inside the screw head 53 because the screw head is connected to the shielding, and therefore, the screw head 53 constitutes the shielding.

Accordingly, the first male connector 61 is fixed in the sealing screw 50 and connected to the cables 65 which are guided through the fourth through-hole 51 of the sealing screw 50, the cables 65 being shielded when exiting the sealing screw 50. Furthermore, the cables 65 and the first male connector 61 are glued into the sealing screw 50 by a medical adhesive such that body fluids and bacteria are prevented from passing the through-hole 51, this can also be achieved by other mechanical means such the use of an o-ring.

Second Transmitting Part and Fourth Connector

Figure 15:
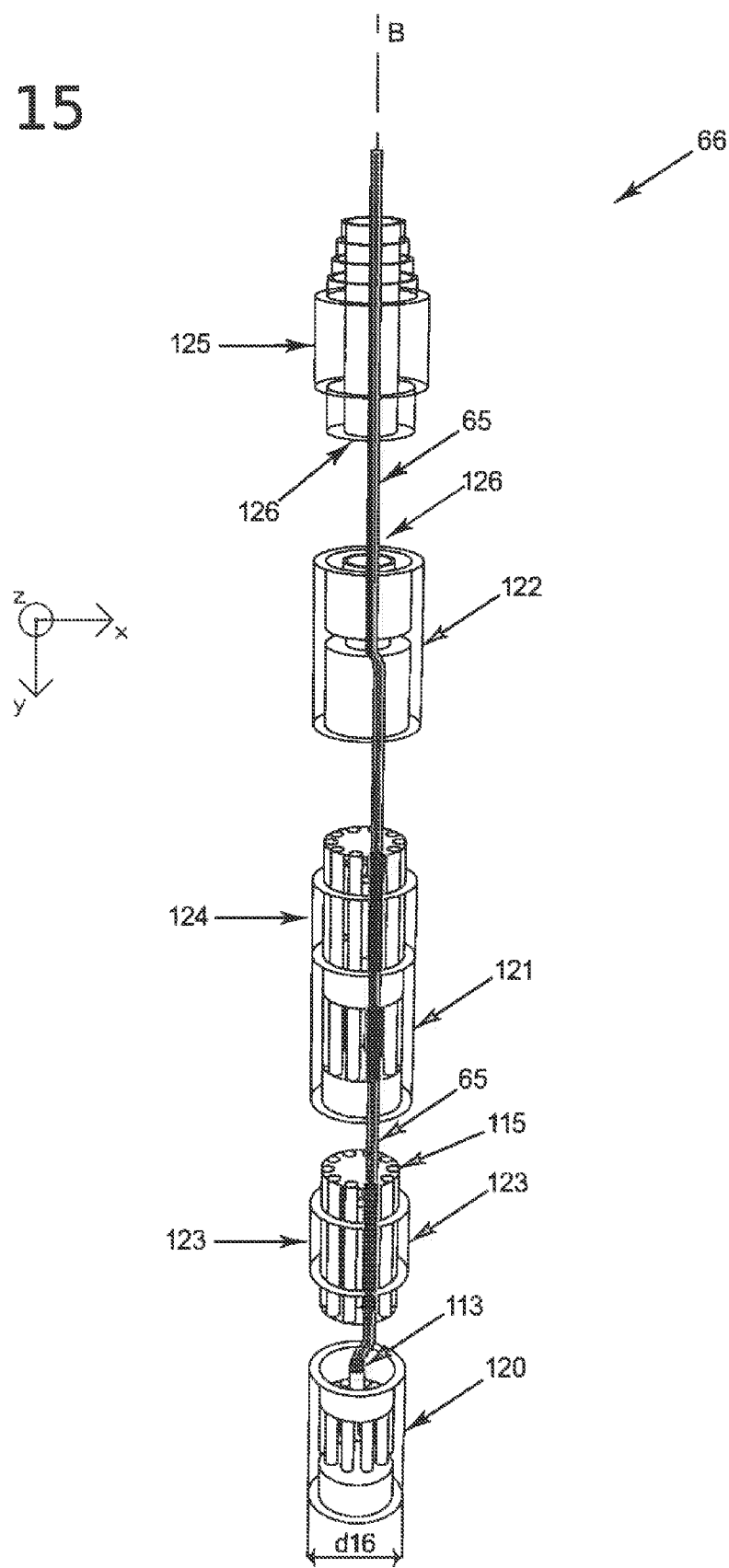
FIG. 15 is a partially cutaway exploded view of a male connector according to the first embodiment.

On the other end of the second transmitting part 22, the shielded cables 65 may end within one or more second in-line male connectors 66 (fourth connector), as shown in FIG. 15.

Each second in-line male connector 66 (fourth connector) may preferably be made of essentially the same material and elements as the first in-line male connector 61. Therefore, only the differences will be described in the following.

The second in-line male connectors 66 may preferably be three-way connectors wherein two male contact elements 120, 121 are used for the signal transfer and one male contact element 122 is used for the shielding. Accordingly, each three-way connector 66 is preferably connected to two signal cables 65. An exemplary course of one cable 65 is shown in FIG. 15. The male or female part of the connector could be change and the number of signals will vary depending on the implanted devices or sensor.

Each second in-line male connector 66 has a first male contact element 120 on the outer end opposite to the cable entrance corresponding to the first male contact element 117 of the first in-line male connector 61. The first male contact element 120 has preferably closed cylindrical through-holes 126 or rather closed channels (see FIG. 15, lower portion). Between the first male contact element 120 and the second male contact element 121, the second in-line male connector 66 preferably comprises a first insulating element 123 made of Silicon or PEEK having the same structure as the insulating element 112 of the first in-line male connector 61. The second male contact element 121 has also the same structure as any one of the intermediate male contact elements 110 of the first male connector 61. Furthermore, a second insulating element 124 corresponding to the insulating elements 112 of the first in-line male connector 61 is provided between the third male contact element 122 and the second male contact element 121.

The third male contact element 122 may differ from the other male contact elements 120, 121. The third male contact element 122 and a third insulating element 125 preferably comprise only one through-hole 126 instead of separate through-holes (channels) for the different cables 65. The inside of the third male contact element 122 is connected to the shielding of the two cables 65 by crimping. The male contact elements 120, 121, 122 and the insulating elements 123, 124, 125 are arranged on a common axis B, shown in FIG. 15. Furthermore, the third insulating element 125 has a gradual tapered end, which facilitates insertion into a female connector 67 and which gives more surface area for the medical adhesive to glue and seal the cables within the tapered end.

Preferably, five of the above second male connectors 66 are provided for transmitting the signals to the first male connector 61. Accordingly, ten different signals may be transmitted by ten male contact elements 110. Furthermore, a maximum outside diameter d15 of the second male connector 66 may be smaller than the minimum inside diameter of the through-hole 11 in the fixture 10a.

May be, the shielded cables 65 have an offset. The offset allows a feed through in series without loosening each of the cables 65 when feeding through. Furthermore, instead of using five parallel connectors 66, one in-line connector having 10 contacts may be used, for example.

Third Transmitting Part and Fifth Connector

Figure 16:
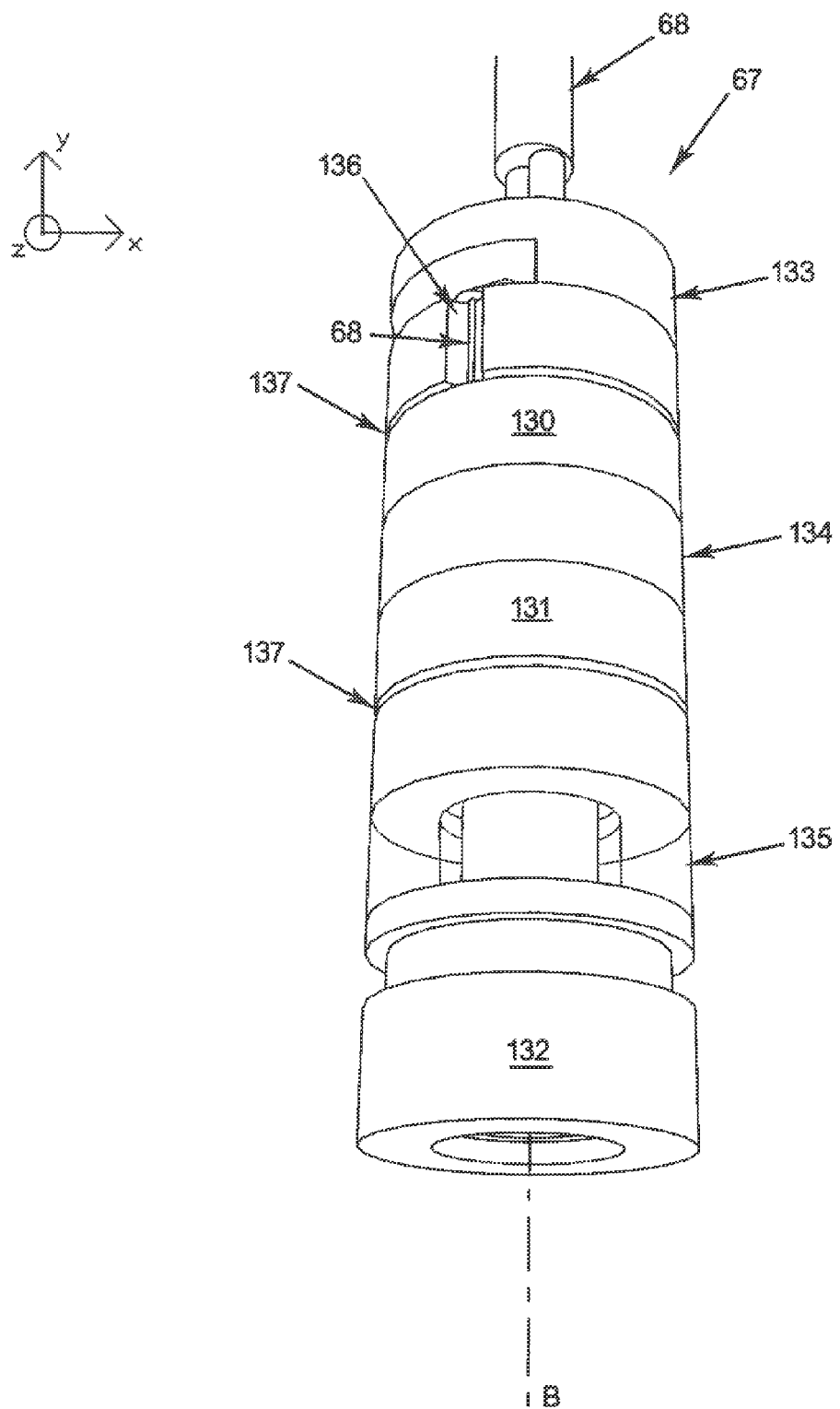
FIG. 16 is a partially cutaway perspective view of a second female connector without insulating and shielding covers according to the first embodiment.
Figure 17:
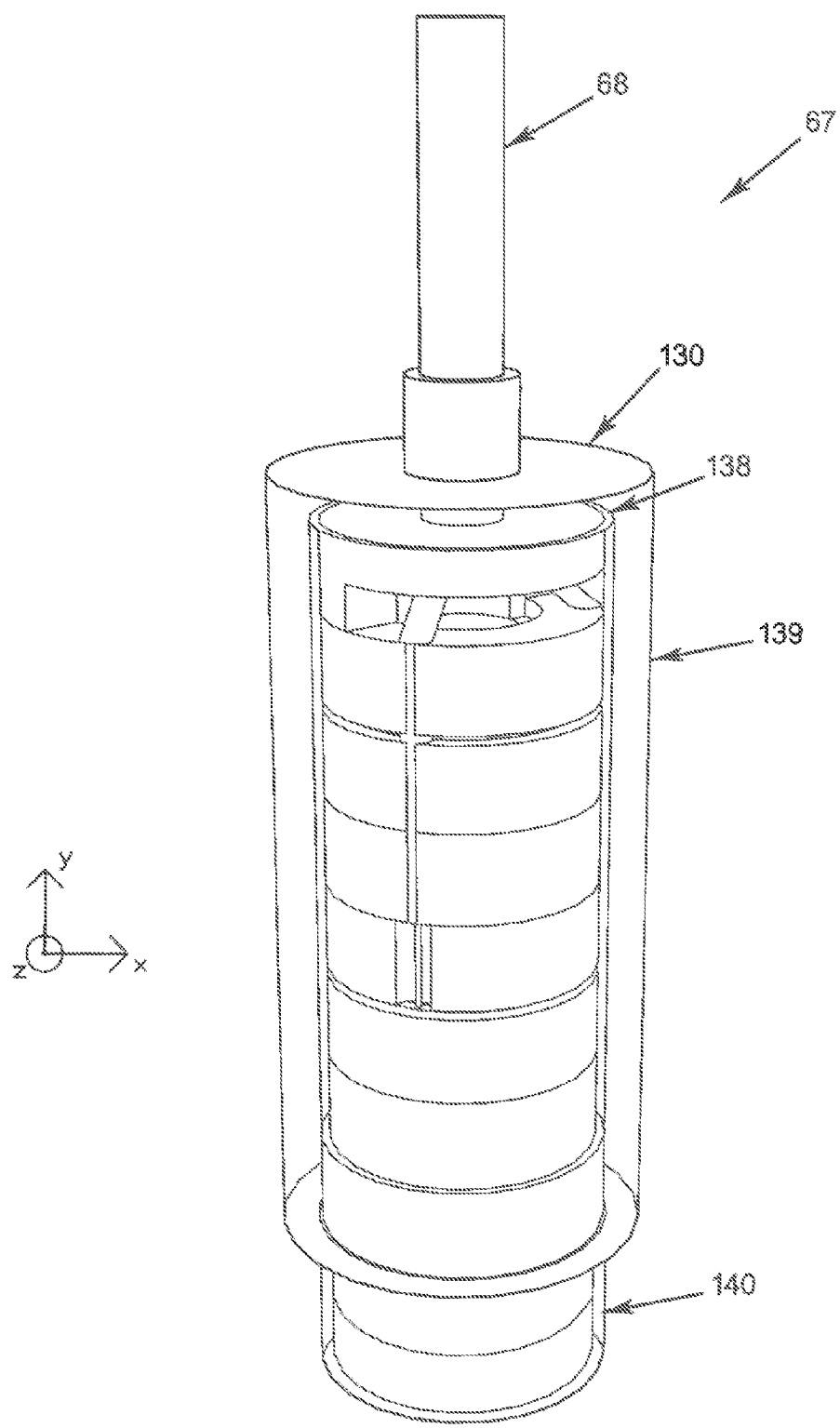
FIG. 17 is a partially cutaway perspective view of the second connector with the insulating and shielding covers according to the first embodiment.

A second longitudinal female connector 67 (fourth connector) is the female part for the above second male connector 66 and shown in FIGS. 16 and 17. The second longitudinal connector is electrically connected to shielded electrode leads 68 (or implanted device leads). The second female connector 67 is preferably made of essentially the same material and elements as the first in-line female connector 71. Therefore, only the differences will be described below.

According to the second male connector 66, the second female connector 67 is a three-way connector wherein the first two contacts sockets 130, 131 are arranged proximate to the electrode leads 68. The first two contacts sockets 130, 131 are used for the signals and the third contact socket 132 is used for the shielding. The three contacts sockets 130, 131, 132 are arranged on the common axis B. Furthermore, a first insulating means 133 may be arranged at the end of the first contact socket 130. A second insulating means 134 may be arranged between the first contact socket 130 and the second contact socket 131, and a third insulating means 135 may be arranged between the second contact socket 131 and the third contact socket 132.

The first contact socket 130 and the second contact socket 131 correspond, basically, to the contact sockets 100 of the first female connector 71. That means, the first contact socket 130 and the first insulating means 133 have, in this embodiment, two grooves or channels 136 on the outer surface in the longitudinal direction B, wherein an electrode lead 68 is guided to the first and second contact socket 130, 131, respectively. Furthermore, the first and second contact sockets 130, 131 preferably comprise an annular groove 137 for electrically connecting the bared portions of the electrode leads 68 to the contact sockets 130, 131 by, for example, welding, according to first female connector 71 but preferably crimping.

The third contact socket 132 is different from the first and second contact sockets 130, 131 and will be explained later. The insulating means 133, 134, 135 and the contact sockets 130, 131 are preferably completely covered by an insulating cover 138, as shown in FIG. 17. This cover 138 has a tubular shape and insulates the outside surface of the contact sockets 130, 131. Furthermore, the whole second female connector 67 is preferably shielded by a shielding cover 139. The shielding cover 139 is preferably crimped to the shielding of the electrode leads 68 at the first end. Furthermore, the shielding cover 139 may be crimped to the third contact socket 132 on the plug-in side (opened side) of the second female connector 67. Therefore, the two contact sockets 130, 131 and the unshielded ends of the electrode leads 68 inside the shielding cover 139, which are guided to the two contact sockets 130, 131, are shielded by the shielding cover 139. Furthermore, the remaining part of the third shielding contact socket 132 is covered by a further insulating and sealing cover 140 on its outside surface. The cover 140 is preferably adapted to seal the inside of the second female connector 67 when the second male connector 66 has been inserted. Furthermore, the crimped connection between the shielded electrode leads 68 and the shielding cover 139 is sealed such that body fluids are prevented from entering into the female connector through the opening for the electrode leads 68.

Therefore, when the second male connector 66 is inserted into the second female connector 67, a shielded and sealed connection is ensured. Furthermore, the tapered end (see reference sign 125) of the inserted male connector 66 may be sealed and glued to female connector 67 by a medical adhesive.

Accordingly, body fluid is preferably prevented from entering into the in-line connectors 66, 67, and the electric signals are transmitted via the first and second male contact elements 120, 121 and contact sockets 130, 131, and the shielding of the cables 65 is transmitted via the third male contact element 122, the third contact socket 132 and the shielding cover 139 to the shielded cable 68.

According to the first embodiment, implanted electrodes 90 that are passively and actively biocompatible are used. Passive biocompatibility refers to the tissue reaction to the composition, shape and mechanical properties of electrode materials. Active biocompatibility refers to the performance of the device under operation. That means, the delivered current should not damage the tissue or cause chemical reactions that form toxic components around the electrode. Electrodes position and signals delivering should be kept constant under dynamical conditions of muscular movements in order to avoid tissue injuries. Accordingly, for example, muscle-based electrodes and nerve-based electrodes, such as needle electrodes, cuff electrodes, micro array electrodes, implantable myoelectric sensors, sieve electrodes, etc, may be used to retrieve the signals or information or to send stimulation pulses.

Assembling of the Percutaneous Gateway Including the Fixing System According to the First Embodiment The assembling steps of the percutaneous gateway including the fixing system according to the first embodiment are explained in the following. At first the stump is incised and a hole for the fixture 10a is drilled into the bone 1. Furthermore, the fixture 10a may be screwed/inserted in the hole of the bone 1 and the incision may be closed. After about six months, the fixture 10a has preferably healed into the bone 1 (osseointegration).

Next, the incision may be re-opened again, i.e. the through-hole 11 of the fixture 10a is re-opened. Afterwards, a drill may be inserted into the through-hole 11 and fed through to the inner end 14 of the fixture 10a ending in the bone 1. Then, a through-hole 80 may drilled from the inner end 14 inside of the bone 1 to its surface. Accordingly, the through-hole 80 may be inclined relative to the central axis A of the fixture 10a.

Afterwards, the second transmitting part 22 comprising the second male connectors 66, the shielded cables 65 and the sealing screw 50 with the first male connector 61 may be inserted into the fixture 10a and the through-hole 80 of the bone 1. That means, each second male connector 66 may be, for example, pulled through the first through-hole 11 of the fixture 10a and afterwards through the through-hole 80 in the bone 1 by a thin wire which has been inserted before. Because the second male connectors 66 are preferably fixedly connected to the shielded cables 65 and the sealing screw 50 with the first male connector 61, the shielded cable 65 and the sealing screw 50 with the first male connector 61 are inserted into the fixture. Accordingly, the second male connectors 66 are firstly fed through the fixture 10a, and thereafter, through the through-hole 80 in the bone 1. It is preferred that the connectors 66 are pulled through, in series (one after another), because this allows them to pass the smallest diameter not at the same time.

Therefore, it may be necessary that the second male connector 66 has a smaller maximum outside diameter d16 than the minimum inside diameter d2 of the through-hole 11, that is, the outside diameter d16 may be smaller than the second female thread 13 of the fixture 10a. Furthermore, also the sum of the diameters of the shielded cables 65 has to fit through the second female thread 13. Therefore, also the sum of the cable diameters may be smaller than the second female thread 13 of the fixture 10a.

Afterwards, the sealing screw 50 may be fixed in the fixture 10a by screwing the sealing screw 50 into second female thread 13. Accordingly, the through-hole 11 of the fixture 10a is closed and sealed by the sealing screw 50, and therefore, the portion of the fixture 10a, wherein the hexagonal fitting 33 and the first female thread 12 are located, are sealed from body fluids entering the fixture 10a from the inner end 14.

Afterwards, the abutment 30 may be inserted into the hexagonal fitting 18 of the fixture 10a. The abutment 30 may be fixed in and tensioned to the fixture 10a by screwing-in the abutment screw 40. The connection between the first transmitting part 21 in the abutment screw 40 and the second transmitting part 22 is achieved by inserting and screwing-in the abutment screw 40 because the first female connector 71 accommodates the first male connector 61 fixed in the sealing screw 50 and thereby connects the corresponding male contact elements 110 with the first contact sockets 100. Accordingly, the percutaneous gateway including the fixing system according to the first embodiment is assembled.

Furthermore, the electrodes 90 which are connected to the electrode leads 68 and the second female connectors 67 may be implanted into the soft tissue 5 and connected to nerves and/or muscles. Afterwards, the second male connector 66 may be connected the second female connector 67. That means, the second male connector 66 may be inserted into the second female connector 67 and sealed. Furthermore, the third connector 72 in the abutment screw head 43 is connected to, for example, an amplifier or a control circuitry (not shown) provided on a robotic prosthesis. Accordingly, the control circuitry or amplifiers of the robotic prosthesis may be permanently connected to at least one electrode 90 implanted in the soft tissue 5 without the need for an extra percutaneous passage from the transmitting device 20.

Furthermore, the entire transmitting device comprising the first, second and third transmitting parts is preferably shielded. In particular, the electrode leads 68, the second in-line female connector 67, and therefore, the second in-line male connector 66 are shielded. Furthermore, the cables 65 are shielded cables wherein the shielding is connected to the sealing screw 50. Accordingly, preferably also the fixture 10a is part of the shielding because the sealing screw 50 is connected to the fixture 10a. Therefore, also the abutment 30 and the abutment screw 40 are part of the shielding.

The design, structure and arrangement of the different connectors 61, 66, 67, 71, 72 allow easy plug-in and ensure the insulation of the different contacts from the body fluids. The respective cables are not exposed to high mechanical stress because the fixing system is rigidly connected to the bone 1. The distance from the electrodes 90 to the control circuit or amplifier is approximately the direct way, and therefore, the shortest distance there between.

All components and cables are preferably made from biocompatible, long-term implantable material, and therefore, they can remain permanently implanted in the human body. Electromagnetic interference (EMI) may be avoided, because all connectors and cables are shielded by a corresponding shielding. Each electrode may easily be exchanged in case of an electrode failure, because the electrodes are preferably individually connected to the transmitting device 20 by the plug-in connection.

Second Embodiment

The percutaneous gateway including the fixing system according to a second embodiment is similar to the percutaneous gateway including the fixing system according to the first embodiment. Accordingly, only the differences from the first embodiment will be explained.

In the second embodiment, the side contacts 73 of the head connector 72 of the abutment screw head 43 may replaced by a circular connector 72a, as shown in FIG. 23. In the circular connector 72a, pins or sockets 73a may arranged side by side inside the screw head 43a and directed into the longitudinal direction x. For an electrical connection to, for example, an amplifier or control circuit, a cable with a corresponding plug or socket may be inserted and fixed in the circular connector 72a.

A circular head connector 72a, according to the second embodiment, allows a sealed and stable electrical connection. Furthermore, such a circular plug/socket 72a is a known standard industrial product, and therefore, has a low price.

Third Embodiment

The percutaneous gateway including the fixing system according to a third embodiment is similar to the percutaneous gateway including the fixing system according to the first embodiment. Accordingly, only the differences from the first embodiment will be explained.

In the third embodiment, the abutment screw 40b may have a kind of circular in-line connector as shown in FIG. 18. That means, the abutment screw head connector 72b (third connector) may be provided with a number of contact rings 73b arranged in parallel and around the cylindrical surface or side surfaces of the head 43b of the abutment screw 40b.

Additionally or alternatively, the internal first in-line female connector 71 may be replaced by a first connector 71b having a cylindrical design similar to a standard head phones connector, as shown in FIG. 18a) and b). That means, the first connector 71b may be configured by, for example, four cylindrical contact rings 100c. The first cylindrical contact ring 100c may have the smallest diameter and protrude furthermost outside the abutment screw 40b. The second cylindrical contact ring 100c may have a larger diameter than the first cylindrical contact ring 100c and protrude not such far as the first cylindrical contact ring 100c. Accordingly, the third cylindrical contact ring 100c may have a larger diameter than the second cylindrical contact ring 100c and protrude less far as the second cylindrical contact ring 100c. Accordingly, the fourth cylindrical contact ring 100c may have the largest diameter and the shortest protrusion.

The advantage of such a cylindrical design according to the second embodiment is the low price because the elements are well-known industrial standard products which may be easily integrated into the abutment screw 40b.

Figure 20:
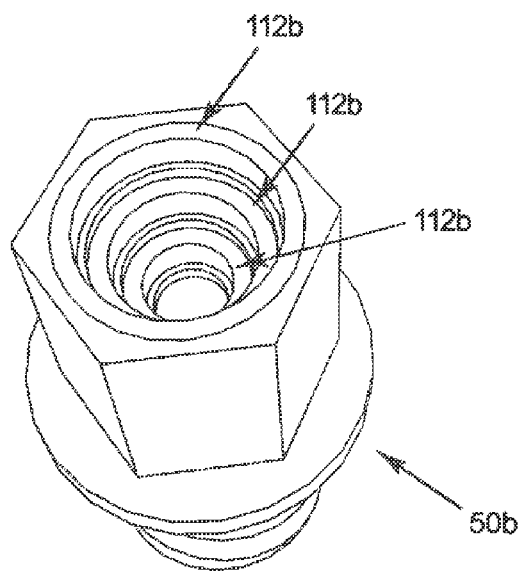
FIG. 20 shows a perspective view of a sealing device according to the third embodiment.

According to the plug design of the first connector 71b, the sealing screw 50b may be adapted to this design. As shown in FIG. 20, the sealing screw 50b may not comprise the in-line male connector 61 but a kind of female socket adapted to the head phone plug design of the abutment screw 40b explained above. Accordingly, different contact rings 112b with different diameters and different protrusion heights may be arranged inside the head of the sealing screw 50b. The contact ring 112b with the largest diameter may be the outermost contact ring.

However, the number of contact is limited regarding the diameter in this embodiment.

Fourth Embodiment

The percutaneous gateway including the fixing system according to a fourth embodiment is similar to the percutaneous gateway including the fixing system according to the first embodiment. Accordingly, only the differences from the first embodiment will be explained.

According to the fourth embodiment, the abutment screw 40c, shown in FIGS. 19a) and b), may comprise an inserted longitudinal feedthrough element 49c with a parallel connector 71c having parallel contacts 100c on the inner end of the abutment screw 40c. In FIGS. 19a) and b), the assembled abutments screw 40c with the inserted feedthrough element 49c is shown on the left side, respectively. In the middle portion of FIGS. 19a) and b), the removed feedthrough element 49c is shown, and on the right side, the abutment screw 40c without the feedthrough element 49c is shown.

The feedthrough element 49c is adapted to be inserted in the abutment screw 40c. The feedthrough element 49c may comprise, as the head connector 72c, for example, contact sockets 73c arranged side by side, as shown in FIG. 19b). Furthermore, the feedthrough element 49c may comprise as a first connector 71c contact pins 100c arranged side by side, as shown in FIG. 19a). The contact sockets 73c and the contact pins 100c are connected by, for example, corresponding cables (not shown) inside the feedthrough element 49c.

Figure 21:
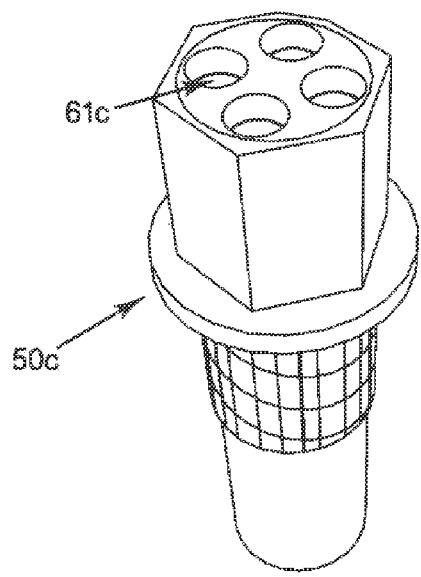
FIG. 21 shows a perspective view of a sealing device according to the fourth embodiment.

Accordingly, the sealing screw 50c may be adapted to the design of the abutment screw 40c with the feedthrough element 49c. Therefore, as shown in FIG. 21, the sealing screw 50c comprises, for example, the corresponding contact sockets 61c.

When inserting the abutment screw 40c comprising the feedthrough element 49c into the fixture, a resistance force may occur, because the abutment screw 40c will twist against the feedthrough element 49c when the feedthrough element 49c is plugged into the corresponding contact socket 61c. Accordingly, as a further possibility (not shown), the outside surface of the feedthrough element 49c may comprise a male thread, and the inside surface of the abutment screw 40c may comprise a female thread. Therefore, at first the feedthrough element 49c is inserted and plugged into the connector (contact sockets 61c) of the sealing screw 50c. Afterwards, the abutment screw 40c may be screwed into the first female thread 12 of the fixture 10a. Thereby, the abutment screw 40c may also be screwed on the male thread of the feedthrough element 49c. Accordingly, the resistance force may be reduced.

Further Embodiments

Figure 22:
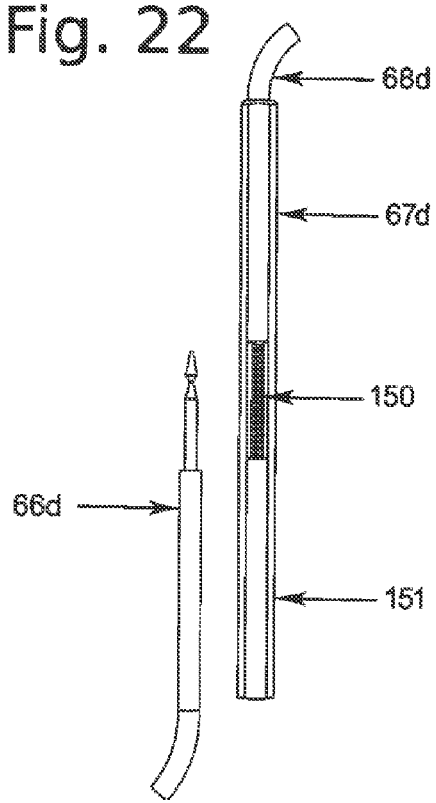
FIG. 22 shows a perspective view of a one-way in-line connector according to a further embodiment.

As another further possibility also the in-line connectors 66, 67 may be replaced by several one way in-line connectors 66d, 67d as shown in FIG. 22. The female connector 67d may comprise a spring 150 connected to electrode lead 68d and a silicon cuff 151. The spring 150 assures electrical contact at the same time that it prevents displacements and allows flexibility. The spring 150 is built in the insulation cuff 151 and its inside diameter should be slightly smaller or equal to the diameter of the male pin 66d. Accordingly, the spring 150 opens slightly with the entrance of the male pin 66d causing enough force to assure electrical contact and retention. Sutures may be done at the end to assure insulation.

Furthermore, the through-hole 11 in the fixture may not extend parallel to the longitudinal axis A of the fixture 10a. That means, the through-hole may end in an intermediate portion (second section) of the fixture in a side wall into to the bone 1. Accordingly, the through-hole 80 in the bone 1 may be orthogonal to the fixture axis. Accordingly, drilling the through-hole 80 into the bone 1 may be simplified because the through-hole 80 in the bone 1 may drilled from outside of the bone 1.

Furthermore, the above disclosed modifications may be combined in different ways.

Materials

For ensuring the ability for a long-term implantation, the shielded cable may additionally covered by a tube made of a long-term biocompatible material. The unshielded cables 75 may have the same material but the shielding is removed.

In particular, the cables 65 may be of stranded wire having improved flexibility. The insulating material is preferably made of long-term implantable material.

The adhesive could be also used as a sealing agent between the respective contacts, insulations and covering tubes, etc.

The insulating means (body fluids and so on) may be made of PEEK or long-term implantable Silicon.

Modifications

Dimensions may be varied in different ways according to the bone size. Furthermore, also the male and female connectors 71, 72, 73, 61, 66, 67 may be interchanged, e.g. the first female connector 71 may be a male connector, and the first male connector 61 may be a female connector, for example.

The contact sockets may replaced by standard sockets having no wire sleeve inside. Instead, the male contact element may have a spring portion contacting the inner surface of the contact socket.

The male connector 61, 66 may not comprises the circularly arranged grooves or channels for guiding the respective transmitting cables, and therefore, each male contact element 110, 130, 131 may not comprise the central crimping contact 113. Instead, the male connector may comprise only one central through-hole 111, and each cable 65 may crimped to a metal element which is welded to the respective male contact element 110, 130, 131 afterwards.

The cables are not limited to be separate cables, but also an integral multi-core cable may be used.

The design of the different elements may be adapted to different bone shapes. That means, the fixture may be adapted to a very flat bone. Accordingly, the length of the fixture will be smaller than the diameter. Furthermore, the sealing screw may not a screw but a plug which is inserted and fixed by an adhesive etc.

Furthermore, the fixing system and fixture are not limited to be used in robotic prosthesis. Also conventional bone anchored prosthesis may make use of the fixing system.

The through-hole 70 inside the bone may also drilled from outside the bone to the inner end of the fixture.

The abutment fixing device 40 (abutment screw) may be countersunk in the abutment. That means, the head of the abutment screw may be inserted in a recess formed inside the abutment head (terminal) 32 such that the head 43 of the abutment screw 40 may not project from the abutment 30.

The fixture may comprise more than one straight through-hole. That means, several parallel through-holes may be provide or one or more branched through-holes are provided. Furthermore, the through-hole may exit the fixture inclined to the longitudinal axis into the bone.

The sealing device may be formed only by, for example, feedthrough contacts. That means, a sealing screw is omitted and replaced by an embedded transmitting device in the implant, i.e. the fixture.

The abutment fixing device may be replaced by, for example, embedding or screwing the abutment into the fixture.

Different devices (electric circuits, amplifiers, etc) may be housed in the percutaneous gateway.

The surgery steps may be interchanged, in particular, the transmitting device and electrodes may be inserted together with the fixture.

Instead of using wires for the different transmitting parts, the cables 75, 65, 68 may be replaced by any other signal transmitting devices as, for example, a fiber optic cable.

It is explicitly stated that all features disclosed in the description and/or the claims are intended to be disclosed separately and independently from each other for the purpose of original disclosure as well as for the purpose of restricting the claimed invention independent of the composition of the features in the embodiments and/or the claims. It is explicitly stated that all value ranges or indications of groups of entities disclose every possible intermediate value or intermediate entity for the purpose of original disclosure as well as for the purpose of restricting the claimed invention, in particular as limits of value ranges.

The invention shall not be considered limited to the embodiments illustrated, but can be modified, combined and altered in many ways by one skilled in the art, without departing from the scope of the appended claims.

The invention claimed is:

1. An apparatus comprising an anchoring element for fixation in a bone tissue, the anchoring element defining a longitudinal axis, and the anchoring element comprises at least one first through-hole substantially extending in the direction of the longitudinal axis, and the anchoring element comprises first attachment means for attaching the anchoring element to the bone tissue and second attachment means for directly or indirectly attaching the anchoring element to a prosthetic limb, the anchoring element comprising at least one seat provided in the first through-hole and the seat being adapted to receive and hold a sealing device adapted to be positioned in the first through-hole, the sealing device being adapted to divide the first through-hole into at a first compartment and a second compartment, and the sealing device being adapted to separate the first compartment from the second compartment in a sealing manner.

2. An apparatus according to claim 1 wherein the first through-hole has an inner wall, at least a portion of the inner wall forms the seat, and the sealing device is adapted to be attached to the inner wall of the first through-hole forming a removable feedthrough connection.

3. An apparatus according to claim 2 wherein the apparatus comprises first signal transmission connection means for connection to first signal transmission means adapted to extend in the first compartment, and in that the first signal transmission connection means is connectable to second signal transmission means adapted to extend in the second compartment and to extend from the sealing device to second signal transmission connection means for connection to at least one implantable component.

4. An apparatus according to claim 1, wherein the apparatus comprises first signal transmission connection means for connection to first signal transmission means adapted to extend in the first compartment, and in that the first signal transmission connection means is connectable to second signal transmission means adapted to extend in the second compartment and to extend from the sealing device to second signal transmission connection means for connection to at least one implantable component.

5. An apparatus according to claim 4, wherein the sealing device is adapted to connect the first signal transmission means and the second signal transmission means in a sealing manner.

6. An apparatus according to claim 4 wherein the first signal transmission connection means is adapted to be located in the first compartment.

7. An apparatus according to claim 5, wherein the first signal transmission connection means is adapted to be located in the first compartment.

8. An apparatus according to claim 7, wherein the sealing device defines a longitudinal axis and comprises at least one second through-hole substantially extending in the direction of the longitudinal axis, and in that the first signal transmission connection means is adapted to at least partly engage the second through-hole in a sealing manner.

9. An apparatus according to claim 8 wherein the apparatus comprises an abutment defining a longitudinal axis, the abutment comprises at least one third through-hole substantially extending in the direction of the longitudinal axis, the second attachment means are adapted to attach the abutment to the anchoring element, and the abutment is mountable to the prosthesis.

10. An apparatus according to claim 9 wherein the third through-hole is adapted to house at least a part of the first signal transmission means extending therethrough from the first signal transmission connection means to a third signal transmission connection means for connection to the prosthesis.

11. An apparatus according to claim 4, wherein the sealing device defines a longitudinal axis and comprises at least one second through-hole substantially extending in the direction of the longitudinal axis, and in that the first signal transmission connection means is adapted to at least partly engage the second through-hole in a sealing manner.

12. An apparatus according to claim 1, wherein the apparatus comprises an abutment defining a longitudinal axis, the abutment comprises at least one third through-hole substantially extending in the direction of the longitudinal axis, the second attachment means are adapted to attach the abutment to the anchoring element, and the abutment is mountable to the prosthesis.

* * * * *